US006770274B1

(12) United States Patent
Martuza et al.

(10) Patent No.: US 6,770,274 B1
(45) Date of Patent: Aug. 3, 2004

(54) VIRAL MUTANT HSV MEDIATED DESTRUCTION OF NEOPLASTIC CELLS

(75) Inventors: Robert L. Martuza, Chevy Chase, MD (US); Donald M. Coen, Medfield, MA (US)

(73) Assignees: The General Hospital Corporation, Boston, MA (US); The President and Fellows of Harvard College, Boston, MA (US)

(*) Notice: Subject to any disclaimer, the term of this patent is extended or adjusted under 35 U.S.C. 154(b) by 1825 days.

(21) Appl. No.: 08/272,516

(22) Filed: Jul. 11, 1994

Related U.S. Application Data

(63) Continuation of application No. 07/868,381, filed on Apr. 14, 1992, which is a continuation-in-part of application No. 07/582,057, filed on Sep. 14, 1990, now abandoned.

(51) Int. Cl.[7] .................... A01N 63/00; A61K 48/00; A61K 31/70
(52) U.S. Cl. .................. 424/93.2; 424/93.6; 514/44
(58) Field of Search .................. 435/172.1, 5, 320.1, 435/172.3, 240.2; 514/44; 424/230.1, 231.1, 233.1, 93.1, 93.2, 93.6

(56) References Cited

U.S. PATENT DOCUMENTS

| 4,883,662 A | * 11/1989 | Stout |
| 6,172,047 B1 | 1/2001 | Roizman et al. ............... 514/44 |
| 6,340,673 B1 | * 1/2002 | Roizman et al. ............... 514/44 |

FOREIGN PATENT DOCUMENTS

| WO | WO 88/09383 | * 12/1988 |
| WO | WO 96/00007 | * 1/1996 |

OTHER PUBLICATIONS

Cowan et al. (1990) "Inhibition of Rate of Tumor Growth in Rodent Species by Inoculation of Herpesviruses and Encephalomyocarditis Virus," J. Med. Viol. 20, 211–215.*
Dubbs et al. (1964) "Mutant Strains of Herpes Simplex Deficient in Thymidine Kinase–Inducing Activity," Virol. 22, 493–502.*
Lorence et al. (1988) "Newcastle Disease Virus as an Antineoplastic Agent: Induction of Tumor Necrosis Factor–alpha and Augmentation of its Cytotoxicity," J. Natl. Cancer Inst. 80(16), 1305–1312.*
Markert et al. (Apr. 1993) "Reduction and Elimination of Encephalitis in an Experimental Glioma Therapy Model with Attenuated Herpes Simplex Mutants that Retain Susceptibility to Acycolvir," Neruosurgery 32(4), 597–603.*
Moore et al. (1952) "Viruses with Oncolytic Properties and their Adaption to Tumors," Annals N.Y. Acad. Sci. 54, 945–952.*
Shimizu et al (1988) "Immunotherapy of Advanced Gynecologic Cancer Patients Utilizing Mumps Virus", Cancer Detection & Prevention 12, 487–495.*

Webb et al (1970) "Viruses in the Treatment of Cancer," The Lancet 1, 1206–1209.*
Fleming Jr., Herpes Simplex Virus Mutants Resistant to Arabinosyladenine in the Presence of Deoxycoformycin:, Sep. 1984, Antimicrobial Agents and Chemotherapy, vol. 26 No. 3, pp. 382–387.*
Field et al, "Pathogenicity of Herpes Simplex Virus Mutants Containing Drug Resistant Mutations in the Viral DNA Polymerase Gene", Oct. 1986, Journal of Virology, vol. 60, No. 1, pp. 286–289.*
Thompson et al, "Herpes Simplex Virus Neurovirulence and Productive Infection of Neural Cells Is Associated with a function Which Maps between 0.82 and 0.832 Map units on the HSV Genome", 1989, Virology vol. 172, pp. 435–450.*
Coen et al (1989) Proced. Natl. Acad Sci. 86, 4736–4740.*
Coen et al (1989) J. Virol. 53, 477–488.*
Chou et al (1990) Science 250, 1262–1266.*
Thompson et al (1989) Virol. 172, 435–450.*
Thompson et al (1983) Virol. 131, 171–179.*
Gibbs et al (1988) Proced. Natl. Acad. Sci. 85, 6672–6676.*
Vieweg et al. (1995) Cancer Invest. 13, 193–201.*
Garrett et al. Der. Biol. Stand. p205–10 vol. 37 1976 provided as Medline No. 03431072 28065072.*
Skinner et al., *Brit. J. Exp. Pathol.*, 69:495–504 (1988).
Huang et al., *Science*, 242:163–66 (1988).
Coen et al., *J. Virol.*, 41(3):909–18 (1982).
Coen et al., *J. Virol.*, 53(2):477–88 (1985).
Gibbs et al., *Proc. Natl. Acad. Sci. USA*, 82:7969–73 (1985).
Field et al., *J. Virol.*, 60(1):286–89 (1986).
Hall et al., *Virology*, 132:26–37 (1984).
Gibbs et al., *Proc. Natl. Acad. Sci. USA*, 85:6672–76 (1988).
Thompson et al., *Virology*, 172:435–50 (1989).
Thompson et al., *Virology*, 131:171–79 (1983).
Chou et al., *Science*, 250:1262–66 (1990).
Kobayashi, H., *Advances in Cancer Research*, 30:279–99 (1979).
Austin, F.C. et al., *Advances in Cancer Research*, 30:301–45 (1979).
Moore, A.E., "The Oncolytic Viruses," *Progr. exp. Tumor Res.*, 1:411–39 (1960).
Coen, D.M. et al., *Proc. Natl. Acad. Sci. USA*, 86:4736–40 (1989).
Geller, A.I. et al., *Science Reports*, 241:1667–1669 (1988).
Geller, A.I. et al., *Proc. Natl. Acad. Sci. USA*, 87:1149–1153 (1990).
Martuza, R.L., et al., *Science*, 252:854–856 (1991).
Geller, A.I., *Nucleic Acids Research*, 16(12):5690 (1988).
Cassel, W.A. et al., *Cancer*, 18:863–868 (1965).

(List continued on next page.)

*Primary Examiner*—Deborah Crouch
(74) *Attorney, Agent, or Firm*—Sterne, Kessler, Goldstein & Fox P.L.L.C.

(57) ABSTRACT

The present invention is drawn to compositions and methods for selectively killing neoplastic cells. Altered viruses are utilized which are capable of replication in neoplastic cells while sparing surrounding normal tissue.

44 Claims, 10 Drawing Sheets

OTHER PUBLICATIONS

Roenigk, H.H. et al., *Arch. Dermatol.,* 109:668–673 (1974).
Takátsy, GY. et al., *Virology,* 5:395–400 (1958).
Cassel, W.A., *Cancer Research,* pp. 618–622 (1957).
Cassel, W.A. et al., *Cancer,* 52:856–860 (1983).
Burdick, K.H. et al., *Cancer,* 17(6):708–712 (1964).
Moolten, F.L. et al., *J. Natl. Can. Inst. Reports,* 82(4):297–300 (1990).
Moolten, F.L., *Cancer Research,* 46:5276–5281 (1986).
Borrelli, E. et al., *Proc. Natl. Acad. Sci. USA,* 85:7572–7576 (1988).
Hanada, N. et al., *J. Med. Virology,* 29:7–12 (it1989).
Ezzedine, Z.D. et al., *Soc. Neurosci. Abstr.,* 16(1):450, Abstract No. 189.3 (1990).
Short, M.P. et al., *Soc. Neurosci. Abstr.,* 16(1):449, Abstract No. 189.2 (1990).
Baker, et al., *Science,* 246:912–915 (1980).
Friedman, et al., *Cancer Research,* 48:4189 (1988).
Shih, et al., *Vaccine,* 85:177–180 (1985).
Palella, et al., *Molecular Cell Biol.,* 8:457 (1988).
Matz, et al., *J. Gen. Virol.,* 64:2661 (1983).
Smiley, *Nature,* 285:333, (1980).
Coen, *Science,* 234:53 (1986).
Araki, et al., *Gene,* 89:195–202 (1990).
Burk, et al., *J. Viral.,* 62:649–654 (1988).

* cited by examiner

VIRAL MUTANT HSV MEDIATED DESTRUCTION OF NEOPLASTIC CELLS

This application is a continuation of application Ser. No. 07/868,381, filed Apr. 14, 1992, which is a continuation-in-part of U.S. Ser. No. 07/582,057, now abandoned, filed Sep. 19, 1990 the disclosure of which is hereby incorporated by reference.

FIELD OF THE INVENTION

This invention relates to treatment of neoplastic cells using viruses.

BACKGROUND OF THE INVENTION

Cancer is a disease of highly evolved multi-cellular organisms. The disease is best defined by the four characteristics which describe how cancer cells act differently from their normal counterpart. First, in most cases, cancer originates from a single cell which proliferates to form a clone of malignant cells. Second, cancer cells grow autonomously and are not properly regulated by the normal biochemical and physical influences in the cells environment. Third, cancer cells are anaplastic which is the lack of normal coordinated cell differentiation. Fourth, cancer cells develop the capacity for discontinuous growth and dissemination to other body parts which is called metastasis.

The terms cancer, neoplasia and malignancy usually are used interchangeably. The term cancer refers to the full spectrum of malignant neoplasms, of which there are over a hundred known types to affect humans (See Mendelsohn, J., in Harrison's *Principles of Internal Medicine,* ed. Braunwald et al., 1987, McGraw-Hill Inc., New York, p. 421–431). These can be broadly classified into three major types. Malignant neoplasms arising from epithelial structures are called carcinomas and constitute the vast majority of all malignant tumors. Malignant neoplasms that originate from connective tissues such as muscle, cartilage, fat or bone are called sarcomas, and malignant tumors affecting hematopoietic structures (structures pertaining to the formation of blood cells) including components of the immune system, are called leukemias and lymphomas. A tumor is the neoplastic growth of the disease cancer.

Neoplasia is a process by which the normal controlling mechanisms that regulate cell growth and differentiation are impaired resulting in progressive growth. During neoplasia, there is a characteristic failure to control cell turnover and growth. This lack of control causes a tumor to grow progressively, enlarging and occupying spaces in vital areas of the body. If the tumor invades surrounding tissue and is transported to distant sites, the tumor will likely cause death of the individual.

One-third of all individuals in the United States will develop cancer (American Cancer Society Yearly Outlook for 1990). The five year survival rate for these patients has risen to nearly 50% as a result of progress and early diagnosis and therapy of the disease (American Cancer Society Yearly Outlook for 1990). However, cancer remains second only to cardiac disease as a cause of death in this country (American Cancer Society Yearly Outlook for 1990). Nearly 20% of all Americans who die this year will die of cancer (American Cancer Society Yearly Outlook for 1990). Half of these deaths will be due to the three most common types of cancer: lung, breast, and colon.

Recently there has been a rapid expansion of cancer treatments. Even though new treatments are being developed, the need still exists for improved methods for the treatment of most types of cancers.

The preferential killing of cancer cells without deleterious effect on normal cells is the desired goal in cancer therapy. In the past this has been accomplished using a variety of procedures. These procedures include the administration of chemicals, chemotherapy, radiation, radiotherapy, and surgery.

Radiotherapy is a regional form of treatment used for the control of localized cancers (See Devita, V. T., in Harrison's *Principles of Internal Medicine,* ed. Braunwald et al., 1987, McGraw-Hill Inc., New York, p. 431–446). Radiotherapy relies on the fact that some malignant diseases are more susceptible to damage by radiation. This difference in susceptibility depends on normal cells having a higher capacity for intercellular repair than neoplastic cells and the ability of normal organs to continue to function well if they are only segmentally damaged. If surrounding tissue can tolerate twice the radiation dose of a given tumor, then the tumor is radiosensitive. On the other hand, some tumors cannot be treated with radiotherapy. Cancer which extensively involves both lungs cannot be treated effectively with radiation therapy because of the greater radiosensitivity of the surrounding lung tissue (See Devita, V. T., in Harrison's *Principles of Internal Medicine,* ed. Braunwald et al., 1987, McGraw-Hill Inc., New York, p. 431–446).

A more modern approach to the use of radiotherapy involves the use of chemicals as radiosensitizers. Chemicals such as n-ethylmaleimide or a synthesis blocker like buthionine sulfoximine can render cells radio sensitive and hence more susceptible to killing by radiation. These chemicals are in the early phases of development are not yet commercially available (See Devita, V. T., in Harrison's *Principles of Internal Medicine,* ed. Braunwald et al., 1987, McGraw-Hill Inc., New York, p. 431–446).

Surgery is still considered the primary treatment for most early cancers (See Devita, V. T., in Harrison's *Principles of Internal Medicine,* ed. Braunwald et al., 1987, McGraw-Hill Inc., New York, p. 431–446). However, most tumors are operable but not fully resectable. Some tumors that appear resectable have micrometastatic disease outside the tumor field. This leads to a recurrence of the cancer close to the initial site of occurrence. Any cancer showing a level of metatastis effectively cannot be cured through surgery.

Other types of localized therapy (nonsystemic) have been explored. These include local hypothermia (Salcman et al., *J. Neuro-Oncol.* 1:225–236 (1983)), photodynamic therapy (Cheng et al., *Surg. Neurol.* 25:423–435 (1986)), and interstitial radiation (Gutin et al., *J. Neurosurgery* 67:864–873 (1987)). To date these therapies have been met with limited success.

Radiotherapy and surgery offer ways of reducing the tumor mass in specific regions of the body that are accessible through surgical techniques or high doses of radiotherapy. Neither is applicable to the destruction of widely disseminated or circulating tumor cells characteristically present in most patients with cancer. This is the stimulus of the development of systemic treatments of cancer such as chemotherapy.

Chemotherapy involves the administration of toxic compounds systemically to a patient (Chabner, B. A., ed., *Pharmacologic Principles of Cancer Treatment,* Philadelphia, Saunders (1982)). Since cancer cells are growing more rapidly than normal cells, toxic compounds are more cytotoxic to cells undergoing rapid division.

Drug, development for cancer began with the accidental identification of the lymphocytic activity of mustard gas used in World Wars I and II. Nitrogen mustard, an antitumor drug, is a derivative of mustard gas and was used to treat lymphomas in the 1940's (See Devita, V. T., in Harrison's *Principles of Internal Medicine,* ed. Braunwald et al., 1987, McGraw-Hill Inc., New York, p. 431–446). Most of the early patients treated with nitrogen mustard had subsequent relapses. This was followed by an overwhelming disappointment and skepticism that cancer could be successfully treated with drugs.

The next drug investigated for antitumor activity was methotrexate (See Devita, V. T., in Harrison's *Principles of Internal Medicine,* ed. Braunwald et al., 1987, McGraw-Hill Inc., New York, p. 431–446). Methotrexate, an antimetabolite, was first used successfully against acute childhood leukemia. In some of the early cases where methotrexate was used, remission produced by the drug appeared permanent.

New compounds are constantly being generated and selected both by rational drug design and random screening. There are six major classes of antitumor drugs; alkylating agents, antimetabolites, plant alkaloids, antitumor antibiotics, endocrine agents, as well as some miscellaneous drugs (Myers, C. E., in *Cancer: Principles and Practice of Oncology,* 2d ed., V. T. De Vito et al. (eds.), Philadelphia, Lippincott, 1985, pp. 290–328).

The use of chemicals, even though widespread in use, has proved of limited effectiveness in treating most cancer types. A major limitation of current chemotherapy is that it is effective only against the most rapidly dividing tumor cells. An additional drawback to the use of cytotoxic agents for the treatment of cancer are their severe side effects. These include nausea, vomiting, CNS depression, localized pain, bone marrow depression, bleeding, renal damage, hypo and hyperglycemia and hypersensitivity reactions.

A more modern approach to chemotherapy is to direct the toxic agents to the cancer cells themselves. This has been accomplished experimentally by linking the chemotherapeutic agent to either antibodies or nontoxic molecules that have a higher affinity for the tumor cells than normal cells. These directed toxic therapies are still in an early clinical phase of development and are not commercially available.

Certain types of cancer, for example gliomas, which are the most common primary tumor arising in the human brain, defy the current modalities of treatment. Despite surgery, chemotherapy, and radiotherapy, glioblastoma, the most common of the gliomas is almost universally fatal (Schoenberg, B. S., "The epidemiology of nervous system tumors," in *Oncology of the Nervous System,* M. D. Walker, ed., Boston, Mass., Martinus Nijhoff (1983); Levin et al., "Neoplasms of the Central Nervous System," Chapter 46, pp. 1557–1611, in *Cancer: Principles and Practice of Oncology,* vol. 2, 3rd ed., De Vita et al., eds., Philadelphia, Lippincott Press (1989)).

Malignant tumors of the nervous system are usually fatal, despite recent advances in neurosurgical technique, radiation therapy, and chemotherapy. In particular, high mortality rates persist in malignant medulloblastomas, malignant meningiomas and neurofibrosarcomas, as well as in malignant gliomas.

Therefore, a need exists for the development of a technique that will selectively destroy tumors of the nervous system while sparing normal cells. In general, such treatment could potentially be used universally for the selective destruction of all types of neoplastic cells.

SUMMARY OF THE INVENTION

Compositions and methods are provided for selectively killing neoplastic cells. The method involves infecting neoplastic cells with an altered virus which is capable of replication in neoplastic cells but spares surrounding non-neoplastic tissue. Upon viral infection, the virus destroys infected cells, generally by oncolysis and/or xenogenization.

DESCRIPTION OF THE PREFERRED EMBODIMENTS

Figure 1:
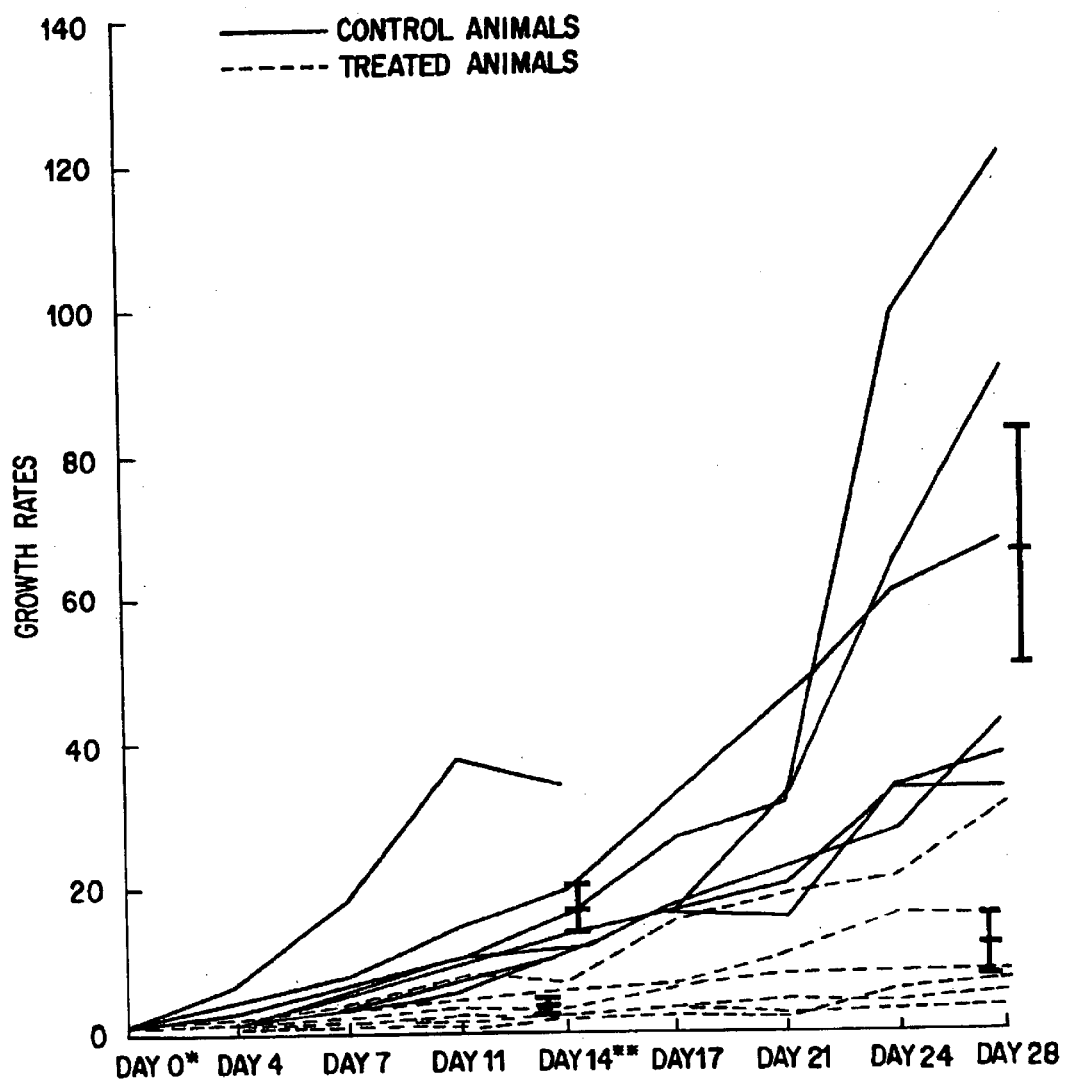
FIG. 1 shows a graph of tumor growth in rats. Nude mice were injected subcutaneously in the left buttock area with $3.2 \times 10^6$ U87 cells. Those animals, having tumors with diameters of approximately eight millimeters after five weeks were then randomly divided into two groups. One group of six animals was injected intraneoplastically with $5 \times 10^6$ pfu of dlsptk in 25 microliters DME. The others received a similar injection of 25 microliters DME alone. Tumor size was monitored via caliper measurement. After two weeks, the tumors were reinjected with $10 \times 10^6$ PFU dlsptk in 50 µl DME or with DME alone.

The present invention is directed to compositions and methods for selectively killing neoplastic cells. In this manner, altered viruses are provided which are capable of replication in neoplastic cells but not normal cells. The viral infection leads to destruction of the neoplastic cells without causing systemic viral infection.

As indicated, the viruses selectively kill neoplastic cells including malignant and benign neoplastic cells. By "neoplastic cells" is intended rapidly dividing cells. For purposes of the invention, neoplastic cells include cells of tumors, neoplasms, carcinomas, sarcomas, leukemias, lymphomas, and the like. Of particular interest are nervous system tumors. These include astrocytomas, oligodendrogliomas, meningiomas, neurofibromas, ependymomas, Schwannomas, neurofibrosarcomas, glioblastomas, etc.

Human and non-human animals suffer from tumors and neoplasms. Specifically, human and non-human animals suffer from nervous system tumors. Thus, the present invention provides a means for treating tumors and neoplasms in animals. More specifically, the present invention provides a means for selectively killing nervous system tumor cells present in animals. By "animals" is intended both human and non-human animals.

Gliomas are the most common primary tumors arising in the human brain. The most malignant glioma, the glioblastoma, represents approximately 30% to 50% of all primary brain tumors and, despite surgery, chemotherapy, and radiotherapy, are almost universally fatal (Moore, A. E., *Progr. Exp. Tumor Res.* 1:411–439 (1960)). The mean survival is less than a year, and the five-year survival rate is only 3% to 5%. After treatment, reoccurrence of the disease often appears within 2 centimeters of the original site (Hochberg et aL, *Neurol.* 30:907–911 (1980)). Metastases are extremely rare; neurological dysfunction and death are due to local growth and cerebral invasion. Therefore, the possible efficacy of local (non-systemic) treatments has been explored. A few of these include studies of local hypothermia (Saloman et al., *J. Neuro-Oncol.* 1:225–236 (1983)), photodynamic therapy (Cheng et al., *Surg. Neurol.* 25:423–435 (1986)), and interstitial radiation (Gutin et al.,*J. Neurosurgery* 67:864–873 (1987)). To date, no therapeutic modality has made a substantial impact on the outcome of patients with malignant gliomas.

Any virus capable of replication selectively in neoplastic cells may be utilized in the invention. Generally, the virus has been altered to render it selective for replication in neoplastic cells. The virus may be altered by mutagenesis as well as genetic engineering techniques.

In general, viruses are defined as infectious units comprising either RNA or DNA enclosed in a protective coat (See Hull, R. et al., in *Virology: Directory and Dictionary of Animal Bacterial and Plant Viruses,* New York, Stockton Press, 1989). The nucleic acid contains information necessary for the replication of the virus in a susceptible host cell. Viruses contain no energy producing enzyme systems, no functional ribosomes, and no cellular organelles. These are supplied by the cell in which the viruses are replicated. The cell may also supply some of the enzymes necessary for viral replication, such as DNA or RNA polymerase and other replication factors.

Methods for mutagenesis are well known in the art. These include a variety of techniques, including chemical mutagenesis (Chu, C. T. et al, *Virology* 98:168 (1979); Myers, R. M. et al., *Science* 229:242 (1985)), oligonucleotide-mediated mutagenesis (Zoller, M. J. et al, *DNA* 3:479 (1984)), and the like.

Alternatively, the virus can be altered by insertion of foreign nucleic acids. In this manner, proteins or factors necessary for viral replication are placed under the control of heterologous promoters and/or heterologous control elements such that the protein is expressed in neoplastic cells only. The heterologous promoters and control elements for the most part are expressed selectively or at a higher level in neoplastic cells. For example, the promoter of a neoplastic gene which is expressed only in neoplastic cells may be utilized. Alternatively, promoters from genes which are expressed at higher levels in rapidly dividing cells, such as thymidine kinase, polymerase genes, etc., may be utilized.

Methods for the construction of engineered viruses are known in the art. Generally these include Sambrook et al., *Molecular Cloning: A Laboratory Manual,* 2nd Ed., Cold Spring Harbor Laboratory Press (1989) and the references cited therein. Virological considerations are also reviewed in Coen D. M, Molecular Genetics of Animal Viruses in Virology, $2^{nd}$ Edition, B. N. Fields (editor), Raven Press, N.Y. (1990) pp. 123–150, and the references cited therein. References drawn specifically to herpes simplex virus 1 (HSV-1) include: Geller et al, *Science* 241:1667 (1988); Geller et al, *Proc. Natl. Acad. Sci. USA* 87:1149 (1990); Geller, A. I., *Nucl. Acid Res.* 16:5690 (1988); Breakfield et al, *Molec. Neurobiol.* 1:339 (1987); Shih et al., in: *Vaccines* 85, Cold Spring Harbor Press, Cold Spring Harbor, N.Y. (1985), pp. 177–180; Palella et al., *Molec. Cell. Biol.* 8:457 (1988); Matz et al., *J. Gen. Virol.* 64:2261 (1983);, Smile J. R., *Nature* 285:333 (1980); Mocarski et al. *Cell* 22:243, (1980); Coen et al., *Science* 234:53 (1986).

As taught by the references, when using heterologous promoters, the gene of interest is placed in the proper reading frame with respect to the heterologous promoter. In this manner, the heterologous promoter directs the transcription of the gene.

For the most part, any virus which is capable of destroying neoplastic cells, and which is capable of being modified for selective replication in such cells, can be utilized. As indicated below, this includes a wide range of viruses which have been used for the treatment of tumors. However, treatment with these viruses has not progressed because of the drawbacks of using unaltered or wild type viruses.

In the past, wild type viruses have been explored as a treatment for the tumors in both animals and in humans (Moore, A. E., *Progr. Exp. Tumor Res.* 1:411–439 (1960); Austin, F. C. et al.,*Ad. in Cancer Res.* 30:301–345 (1979)). The proposed therapeutic mechanisms include oncolysis, direct cell killing by the virus (Moore, A. E., *Progr. Exp. Tumor Res.* 1:411–439 (1960)), and xenogenization the production of new antigens on the tumor cell surface to facilitate an immunological rejection of the tumor (Austin, F. C. et al., *Ad. in Cancer Res.* 30:301–345 (1979); Kobayashi, H. et al., *Ad. in Cancer Res.* 30:279–299 (1979)).

There are several early references to the beneficial effects of viral infection on the progression of malignant diseases (Levanditi, *Ann. Inst. Pasteur* 37:1–106 (1923)). Regressive changes have been noted in various tumor types when the patients have either been deliberately or accidentally infected with a virus. In 1912 regression was observed in a patient with cervical carcinoma undergoing rabies treatment for a dog bite. It was then postulated that a rabies virus may have been the cause of tumor regression (Southom, C. M., *Tran. N.Y. Acad. Sci. Ser.* 2122:653–673 (1960)).

Between 1950 and 1967 there were numerous reports that suggested some patients showed regressive changes in their cancers when treated with viruses (Moore, A. E., *Ann. Rev. Microbiol.* 8:393–410 (1954); Moore, A. E., *Progr. Exp. Tumor Res.* 1:411–439 (1960)). In 1956, the use of viruses to treat carcinoma of the cervix was reported (Smith et al., *Cancer* 9:1211–1218 (1956)). Use of the adeno virus resulted in the slowing of the tumor growth after oncolysis. However, no appreciable modification in the course of the disease was noted. In 1965, the use of Newcastle disease virus for the treatment of cervical carcinoma was attempted (Cassel, W. A. et al., *Cancer* 18:863–868 (1965)). NDV was chosen because it has a very low degree of neurotropism, the ability to infect neural tissues. Direct inoculation of the virus into the carcinoma of the cervix resulted in extensive sloughing of the tumor and the shrinkage of the lymphnode metastasis. The use of NDV was deemed hopeful due to the fact that this patient showed no evidence of a virus attacking the nerve tissues. In 1966, a report of a clinical trial using viruses to treat other cancer was published (Webb, H. E. et al., *Lancet* 1:1206–1209 (1966). The viruses used in this study were Lungat and Kyasanur Forest disease virus.

More recent studies have been published concerning the use of viruses to treat cancers. In 1983, a study was published on the use of the Newcastle disease virus oncolysates in the management of stage II to malignant melanoma (Cassel, W. A. et al., *Cancer* 52:856–860 (1983)). Patients received subcutaneous injections of viral oncolysates over a three year period. Even though these patients were at an advanced stage of disease, stage II, the results suggested an improvement. The mortality rate of 6, 8 and 12 percent in each of the 3 years respectively in the study group was considerably lower than that in the control group. Viral replication is not noted in the study and the effects noted were probably due to the xenogenization of the entire tumor cells.

Roenigle et al. (Roenigle, H. H. et al., *Arch. Dermatol.* 109:668–673 (1974)) report on the positive result of immunotherapy of malignant melanoma with interlesional inoculations of vaccinia virus. Major regression of the tumors were observed in 8 out of 8 patients with stage II disease. In other studies with patients in stage III disease, little or no regression was observed. Additionally, work utilizing vaccinia virus therapy demonstrating positive results has been published (Belisario, J. C. et al., *Aust. J. Derm.* 6:113–118 (1961); Milton, G. W. et al., *Aust. N. Z. J. Surg.* 35:286–290 (1966); Hunter-Craig, I. et al., *Br. Med. J.* 2:512–515 (1970)). These have been performed primarily in patients without extensive tumor involvement.

Several animal models and animal tumors have also been utilized in the study of oncolysis by viruses in tissue culture and in whole animal systems (Moore, A. E., *Ann. Rev. Microbiol.* 8:393–410 (1954); Moore, A. E., *Progr. Exp. Tumor Res.* 1:411–439 (1960)). At least nine viruses have been shown to be capable of causing tumor regression to some degree in a variety of tumors in mice, rats, rabbits, and guinea pigs. However, a major drawback of these early animal studies was systemic infection by the virus used to treat the tumors.

In contrast to prior studies, the present invention utilizes altered viruses. These altered viruses, for the most part, are not capable of replication in certain normal cells, thus reducing the threat of systemic infection. Now that the present invention demonstrates that viruses can be altered to selectively replicate in and kill neoplastic cells, specifically by utilizing a mutant HSV-1 to kill glioma cells, the method can be utilized to alter other viruses such as those discussed above.

In addition to gliomas, the present invention demonstrates that a mutant HSV-1 can selectively replicate in and kill malignant nervous system tumors including medulloblastomas of different differentiation types, malignant or atypical meningiomas, and neurofibrosarcomas. Further, other HSV mutants are provided which are shown to be associated with decreased neurovirulence while retaining cytopathic effects in glioma cells.

Mutant viruses having decreased neurovirulence exhibit a decreased pathogenic effect on normal nervous system cells when compared to corresponding non-mutated or wild-type viruses. For example, the HSV mutants disclosed in the present invention exhibit decreased neurovirulence as compared to normal HSV. In particular, HSV mutants having mutations in the HSV DNA polymerase, thymidine kinase and γ-34.5 genes are provided and are shown to exhibit decreased neurovirulence while retaining cytopathic effects in glioma cells.

Also, intertypic recombinants (HSV-1 and HSV-2) with lesions conferring attenuation mapping to the inverted repeat in the long segment of the HSV genome represent HSV mutants with decreased neuro-virulence which retain cytopathic effects in glioma cells.

Thus, any mutation or alteration in the HSV genome which decreases neurovirulence while maintaining cytopathic effects in nervous system tumors will provide HSV mutants useful for selectively killing cells of nervous system tumors.

The use of viruses in tumor therapy is also beneficial as the virus modifies the tumor cells so that they become more antigenic. See, for example, Araki et al. *Gene* 89:195–202 (1990); Takle et al. *Mol. Biochem. Parasitol* 37:57–64 (1989); and Burk et al. *J. Virol.* 62:649–654 (1988). This antigenic effect is accomplished by introducing new antigens on the surface of the tumor thus augmenting one's immune system in recognizing the tumor as a foreign body. The introduction of new antigens to the surface of the tumor is referred to as xenogenization of tumors (Austin, F. C. et al., *Ad. in Cancer Res.* 303:301–345 (1979); Kobayashi, H. et al., *Ad. in Cancer Res.* 30:279–299 (1979)).

When tumors cells are infected with a virus, they generally express the viral antigen on the cell surface. When the virus used to infect the tumor cells are recognized as foreign to the hosts, then the virus infected tumor cells often undergo regression. Kobayashi (Kobayashi, H. et al., *J. Natl. Cancer Inst.* 42:413–419 (1969)) attempted to promote the tumor rejection in rats with tumors by establishing a viral infection of the host with murine leukemia viruses such as Friend virus or Gross virus. These viruses were believed to produce surfacing antigens on host cells. Success was noted in the immunological regression of these rat tumors. Several other reports have been noted with viral induced regression of transplanted tumors in rats (Holtermann, D. A. et al., *Transplantation* 11:20–29 (1971); Barbieri, D., et al. *Int. J. Cancer* 7:364–371 (1971); Greenberger, J. S. et al., *J. Natl. Cancer Inst.* 51:1935–1938 (1973)).

Successful tumor regression in systems other than rats has been noted. In 1971, it was reported that the lethal growth of mouse tumors was decreased by 46 to 77 percent when the tumor cells were infected with Rauscher leukemia virus (Barbieri, D. et al, *Int. J. Cancer* 7:364–371 (1971)). Holterman and Majde Holtermann, D.A. et al., *Transplantation* 11:20–29 (1971) reported that the lethal growth of a adeno carcinoma in SWR/J mice was decreased 50 percent if the tumor cells were first infected with the LCM virus.

Another study also reported the decrease in the lethal growth of tumors following the infection with the HVJ virus was noted in the Hamster model system (Yamada, T. et al., *Gann.* 63:647–655 (1972)). However, viral growth in the host limited the effectiveness and continuation of this potential therapy.

Virus may also be used to insert new genes into tumor cells which can alter cell growth characteristics or modulate cell growth. An example of this is the insertion of a tumor suppressor gene as has been shown for the Rb gene in retinoblastoma or osteo gene sarcoma (Huang H-JS et al., Suppression of the neoplastic phenotype by replacement if the Rb gene in human cancer cells in *Science* 242: 1563–1566 (1988)) or the p53 gene in colon cancer (Baker et al., Suppression of human colorectal carcinoma cell growth by wild-type p53 in *Science* 249:912–915 1990)). In addition, other suppressor or modulating genes may be used.

Attempts have been made to modify viruses naturally to make them more capable of infecting tumor cells (Moore, A. E., Ann. N.Y. *Acad. Sci.* 54:945–952 (1952); Southam, C. et al., *Virology* 5:395–400 (1958); Cassel, W. A., *Can. Res.* 17:618–622 (1957)). This has been accomplished through serial passages of the viruses through tumor lines in vitro. In most cases where an increase in tumor specificity has been noted a reversion back to the wild type viral infection spectrum was noted after serial passage of virus back into the host organism. It would be more desirable to control specificity in a more reliable fashion than to randomly select for specificity through passaging.

The present viruses, altered by genetic engineering techniques or mutation, are targeted to specific cell types. This targeting may be able to be performed by a variety of techniques.

Tumor specific control elements can be introduced into the virus genome to control the expression of any one or more of the viral genes necessary for viral replication. In doing so the virus would only be able to replicate in cells in which the tumor specific control element was expressed. This would eliminate the potentiality of inducing a systemic viral infection in the host when these viruses are used for cancer treatment.

As an alternative to tumor specific control elements, specific mutations can be introduced into the virus genome such that the virus would be unable to replicate in cells unless the cell provided a complementary enzymatic function. This would lead to a directed infection of the tumor cells only.

After a particular virus has been chosen, it can be tested in vitro for the ability to replicate and suppress or destroy growth of neoplastic cells. The virus is thus altered by mutation or genetic engineering techniques such that the virus will replicate and cause oncolysis and/or xenogenization and/or cell growth modulation in tumor cells while being unable to replicate in normal cells. The virus is then used to establish localized infection within neoplastic cells of a patient.

To effect viral infection, the virus is typically injected into the host at or near the site of neoplastic growth although systemic inoculation may also be feasible if cell-specific viruses are used. Generally, the virus is provided for injection in a concentration in the range of about $10^1$ to about $10^{10}$ plaque forming units (PFU), specifically about $5 \times 10^4$ PFUs to about $1 \times 10^6$ PFU, more specifically about $1 \times 10^5$ PFU to about $4 \times 10^5$ PFU although ranges may vary.

The following examples are offered by way of illustration and not by way of limitation.

EXAMPLE 1

Glioblastomas are the most common form of malignant brain tumors in man, and are almost always universally fatal (Schoenberg, B. S., "The epidemiology of nervous system tumors," in *Oncology of the Nervous System*, M. D. Walker, ed., Boston, Mass., Martinus Nijhoff (1983); Levin et al., "Neoplasms of the Central Nervous System," Chapter 46, pp. 1557–1611, in *Cancer: Principles and Practice of Oncology*, vol. 2, 3rd ed., De Vita et al., eds., Philadelphia, Lippincott Press (1989)). Human malignant glioma cells are a class of rapidly dividing tumor cell population which express enzymes associated with DNA replication. One of these is the enzyme thymidine kinase. The surrounding normal brain is mostly composed of non-dividing cells, such as neurons and normal gila. These cells express enzymes involved in DNA replication at a minimal level. The present invention is directed to take advantage of this phenomenon. A virus, such as Herpes simplex virus 1 is mutated in one of the viral genes, such as the enzyme thymidine kinase. This mutant virus is used to treat the tumor. This is accomplished by the virus's ability to replicate within the malignant glioma cells using the tumor cell's endogenous thymidine kinase activity, to complement the mutation. This leads to the lysis of the tumor cell. In contrast, normal brain cells, which are non-dividing are relatively non-permissive for lytic infection by some mutant viruses and are spared from viral lysis. (Jamieson A T, *J. Gen. Virol.* 24:465 (1974).

The possibility of using a mutant virus to treat human cancer was explored using the virus dlsptk (Coen et al., *Proc. Natl. Acad. Sci. USA* 86:4736 (1989)). This particular mutant was chosen among several possible thymidine kinase mutants of HSV1 because it has no detectable thymidine kinase activity and because it has a large deleted segment. This large deletion makes this virus unable to spontaneously revert to wild-type virus. A third advantage is that the deletion lies outside the HSV UL24 gene, which overlaps the thymidine kinase gene and thus dlsptk should not be impaired for UL24 function. Reported herein are the results of testing dlsptk virus versus five different human gliomas: two in long-term culture and three in short-term culture. Also reported are the results of inoculating dlsptk intracranially into rodents and of the intraneoplastic inoculation of human gliomas grown in two different anatomical locations in nude mice with dlsptk.

dlsptk was deposited under the Budapest Treaty on Apr. 8, 1992 at the American Type Culture Collection located at 12301 Parklawn Drive, Rockville, Md. 20852, USA. dlsptk was assigned ATCC Designation VR 2372.

The human glioma lines U87 and T98G cells were obtained from the American Tissue Cell Collection (ATCC), Camden, N.J. Three primary human malignant glioma cultures were started from explants obtained from surgical specimens at the Massachusetts General Hospital. Vero (African green monkey kidney) cells were obtained from the ATCC. All cell cultures were grown on plastic tissue culture dishes in 5% $CO_2$ at 37° C. using Dulbecco's modified Eagle's medium supplemented with 10% fetal bovine serum and antibiotics (DME).

Viruses were grown and titered on Vero cells as previously described and are recorded as plaque forming units (PFU) per specified volume. Susceptibility to foscarnet and vidarabine were assayed by plaque reduction to demonstrate that dlsptk retained sensitivity to these drugs which have been used in patients to treat serious HSV infection.

All animal studies were done in accordance with guidelines for animal care as defined by both the National Institutes of Health and by the Massachusetts General Hospital Subcommittee on Animal Care. Rats (CDF Fisher male; 150–175 grams) were obtained from Charles River; nude mice were obtained from the breeding colonies at the Massachusetts General Hospital. Each was housed in facilities appropriate for their care. All culture and animal procedures involving viruses were approved by the Harvard Environmental Safety Committee.

KOS is a standard laboratory wild type strain. HSV1-dlsptk was constructed as described by Coen et al., *Proc. Natl. Acad. Sci. USA* 86:4736 (1989). In the example discussed, the sensitivity of the glioma cell lines was tested for infection for KOS and dlsptk. In addition, the effects of intracranial inoculation of KOS and dlsptk were assayed. Finally, the effects of dlsptk on tumors implanted in three different positions of a body of mice were assayed.

In cell culture, either wild type virus KOS or the thymidine kinase negative mutant (dlsptk) was applied to multiplicities of infection (MOI) ranging from $10^{-4}$ to $10^1$ to U87 cells and to Vero cells. With both cell types, the number of cells showing cytopathic effect at 24 hours was directly related to the multiplicity of infection and ranged from 1–5% at MOI=$10^{-4}$ to 95% at MOI=10. At 24 hours after viral application, the extent of cytopathic effect and cell detachment in the U87 cells was equal to or greater than that seen in the Vero cells at equal MOI. By five days following infection, cytopathic effect was 100% for both viruses in both cell types at all MOI$\geq 10^{-1}$; by nine days 100% cytopathic effect was evident even for the plate inoculated with dlsptk at an MOI=$10^{-4}$. This suggested that even at a very low inoculum (an MOI of $10^{-4}$ is equivalent to 10 pfu/culture plate), dlsptk was able to sustain a spreading infection and to destroy the entire monolayer of U87 cells in 9 days.

In order to determine if dlsptk would lyse a different human glioma line in cell culture, T98G and Vero cells were inoculated with dlsptk at an MOI=10. Both viruses produced complete cell destruction of each line within several days.

Since both U87 and T98G are long term lines of human gliomas, the effect of HSV1-dlsptk was determined on primary human gliomas. Monolayer cell cultures were derived by explanating three primary glioma specimens obtained at surgery and studied at the second passage. Following application of dlsptk at MOI=10 or MOI=1, all 3 primary gliomas demonstrated cytopathic effect in a dose dependent fashion. By four days, 100% cell destruction was evident in all 3 cultures at both MOI tested.

In order to establish the safety of intracerebral inoculation of dlsptk, 13 male Fischer rats (150–175 g) stereotactically inoculated in the right frontal lobe with $2 \times 10^5$ pfu HSV-dlsptk in 2 $\mu$l DME and 12 rats with $1 \times 10^6$ HSV-dlsptk in 4.8 $\mu$l DME. Two of the $2 \times 10^5$ pfu group died at the time of anesthesia and surgery. All remaining animals were followed for at least one month following inoculation. There were no deaths or neurologic dysfunction in either group. The $2 \times 10^5$ pfu group were allowed to live an additional month before sacrifice. At two months, all were healthy and showed no evidence of neurologic dysfunction nor cataracts. This is in contrast to prior studies by Chiocca et al. showing that a similar dose of the wild type virus (KOS, $2 \times 10$ pfu) killed 718 rats within two weeks after intracranial inoculation.

To test the effects of HSV-dlsptk on U87 tumors in vivo, a group of 17 nude mice were injected subcutaneously in the left buttock area with $3.2 \times 10^6$ U87 cells. Growing tumors were evident at approximately 5 weeks. 12 animals had tumors with diameters of greater than 8 mm. These were randomly divided into two groups. Using a bevel tip Hamilton syringe, one group of 6 animals received an intraneoplastic inoculation of $5 \times 10^6$ pfu HSV1-dlsptk in 25 $\mu$l DME. The control group of 7 received a similar inoculation of DME alone. After two weeks the tumors were reinjected with twice the dose. The tumors receiving injections of dlsptk were significantly smaller than the controls after 2 and 4 weeks of measurement (FIG. 1).

Figure 2:
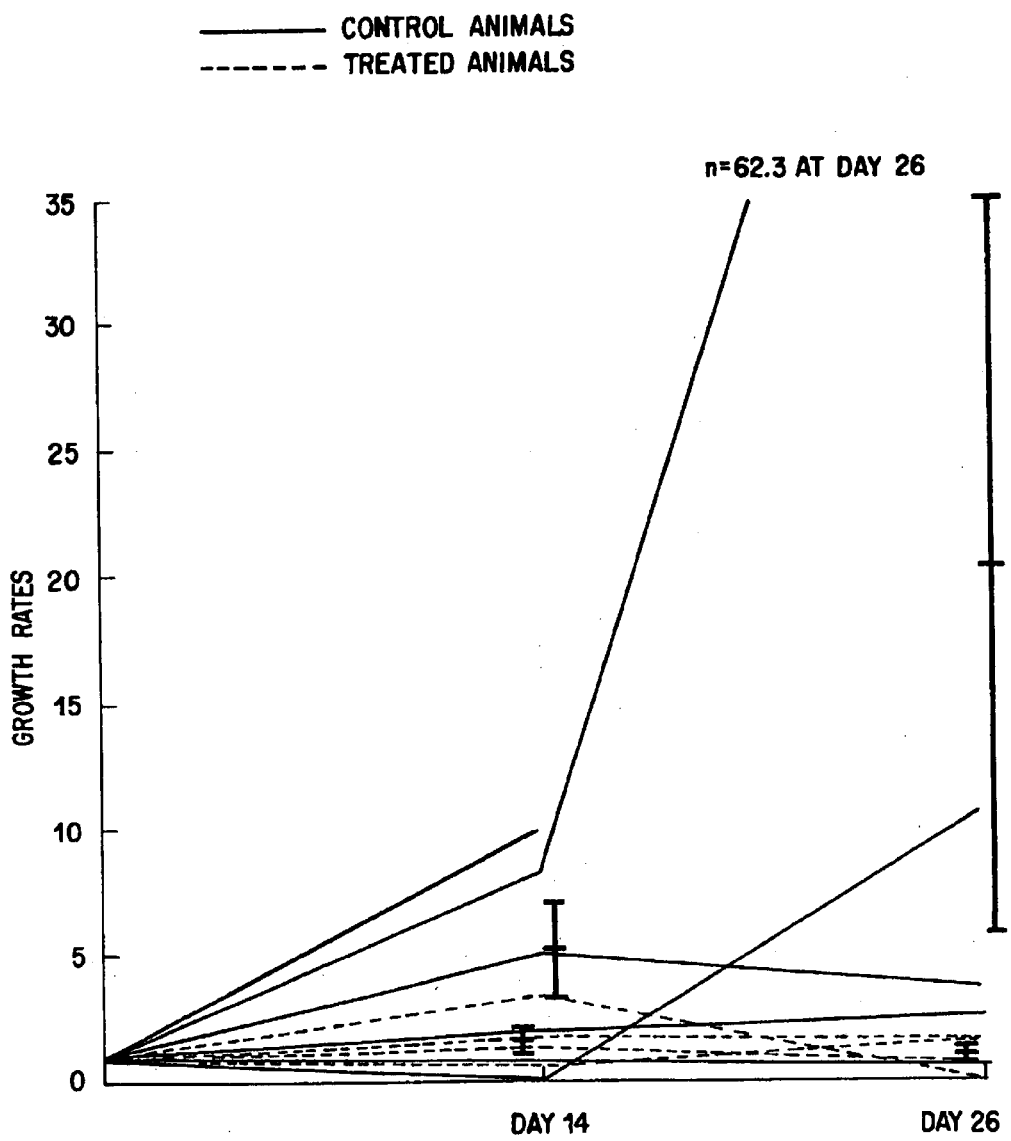
FIG. 2 shows that at day 14 and day 26 after inoculation the dlsptk treated tumors were significantly smaller than the control tumors.

The effectiveness of dlsptk was also tested at a second location. Nine nude mice were inoculated in the subrenal capsule with U87 cells using the fibrin clot technique previously described. After 2 weeks, tumor sizes were measured with an ocular micrometer and found to be 1 to 2 mm in diameter. Half the animals were inoculated intraneoplastically with 1 $\mu$l DME and the other half were inoculated intraneoplastically with 1 $\mu$lDME containing $2.1 \times 10^5$ pfu HSV-dlsptk. FIG. 2 shows that at reexploration at day 14 and day 26 after inoculation, the dlsptk treated tumors were significantly smaller than the controls.

To evaluate the efficacy of dlsptk in treating intracerebral gliomas, we stereotactically inoculated 20 nude mice in the right frontal lobe and with $1.6 \times 10^5$ U87 cells, a cell inoculum that in a pilot study caused 100% mortality within 1.5 months. After 10 days, the animals were divided randomly into three groups. One group received $10^3$ pfu of dlsptk, a second group received $10^5$ pfu of dlsptk, and controls received DME+alone. Inoculations were in 2 $\mu$l DME+ at the stereotactic coordinates initially used to inject the U87 cells. By week 7, all six controls were dead. In contrast, three of seven (43%) of the $10^3$ pfu group were alive and four of seven (57%) of the $10^5$ pfu group were alive. By week 14, all seven of the $10^3$ pfu group were dead, but two of seven (29%) of the $10^5$ pfu group were alive. These two animals were still healthy and neurologically normal at week 19, at which time they were killed. The entire brain was then fixed, serially sectioned at 7-$\mu$m intervals, stained with hematoxylin and eosin, and microscopically examined. Some evidence of encephalitis with scattered foci of lymphocytic infiltration in the meninges and brain was noted, but no definite evidence of tumor could be found in either brain.

EXAMPLE 2

The efficacy of HSV1-dlsptk (as shown in Example 1) against malignant human gliomas suggested that genetically-engineered viruses could have therapeutic potential for other neoplasms.

Specifically, the effects of HSV1-dlsptk treatment in medulloblastoma, malignant and atypical meningioma, and neurofibrosarcoma were examined.

Materials and Methods

Cell Lines and Tumor Explants

The human medulloblastoma cell lines Daoy, D283 Med, (from ATCC), and SNB40 were used for the in vitro assay; Daoy and SNB40 grow in monolayer and possess glial-type differentiation, while D283 Med grows in suspension and possess neuronal characteristics. Four neurofibrosarcoma cell lines were obtained and grown in monolayer. All meningiomas (one atypical, two malignant,and one malignant, hemangiopericytic type) and one neurofibrosarcoma were obtained as tumor specimens and started in culture. Techniques and maintenance were as previously described (See Martuza et al. *Science* 252:854 (1991)).

In Vitro Assay of Cytotoxicity

Multiplicity of infection (MOI) was calculated from cell number as described (See Martuza et al. *Science* 252:854 (1991)). The appropriate number of viral plaque forming units (pfu) was applied and distributed evenly. All viral-infected plates were compared to control plates (DME+ only, no virus). Cells were then maintained as described (See Martuza et al. *Science* 252:854 (1991)) and observed microscopically; cells that had rounded, losing normal morphology, as well as lifting from the plate, were considered dead. Monolayers were completely destroyed when $\geq 99\%$ of the cells exhibited cytopathic effects. No destruction was exhibited in control plates unless specifically mentioned. The viability of D283 Med cells, the single cell type used which grows in suspension, was assessed via the trypan blue exclusion method. Samples were diluted one part cell suspension to three parts 0.1% solution of trypan blue and percent viability assessed microscopically via hemocytometer.

Animals

Female athymic BALB/c mice (nu/nu genotype, approximately six to ten weeks of age) were used for in vivo studies and maintained as previously described (See Martuza et al. *Science* 252:854 (1991)).

Xenograft Transplantation

The Daoy medulloblastoma was chosen for in vivo studies (Friedman et al., *Cancer Res.* 48:4189 (1988)). Other cells used for in vitro studies in this investigation proved inappropriate due to insufficient in vivo growth. Subcutaneous xenograft transplantation was performed as previously described (See Martuza et al. *Science* 252:854 (1991)). Daoy cells in suspension ($1 \times 10^7$ cells in DME+) were injected subcutaneously into a host mouse. After five weeks, the host mouse was humanely sacrificed and the tumor minced into 1 mm pieces, which were transplanted subcutaneously into additional mice.

Subcutaneous Tumor Measurements

Tumors were measured twice weekly with Vernier calipers until week 4, then weekly thereafter, as previously described (See Martuza et al. *Science* 252:854 (1991)).

Tumor Therapy

Subcutaneous tumors were allowed to reach a minimum diameter of 6 mm. They were then directly inoculated with $10^7$ pfu of virus suspended in 0.05 ml DME+ via tuberculin syringe (n=8). Care was taken to distribute virus throughout the tumor. Controls (n=9) were treated in a similar fashion with DME+ alone. Treatment was repeated in an identical fashion on day 10. Growth of subcutaneous xenografts was recorded as the tumor growth ratio, utilizing the formula $((1 \times w \times h)/2)/((1 \times w \times h)_{day\ 0}/2)$ as previously described (See Martuza et al. *Science* 252:854 (1991)). Additionally, the number of treated versus control tumor regressions was analyzed. Potential differences in growth ratios were assessed utilizing the one-sided Wilcoxon rank test, while number of regressions were compared by Fisher exact test.

Results

In Vitro Cytotoxic Assays

Medulloblastoma

The monolayer medulloblastoma cell lines studied, Daoy and SNB40, were tested at two different MOIs, $10^{-1}$ and $10^{-3}$. At an MOI of $10^{-1}$, complete monolayer destruction was present by day 4; at $10^{-3}$, complete destruction took from 4 to 11 days.

The suspension medulloblastoma line, D283 Med, was tested at higher MOIs of 1 and 10 due to the barrier to ordinary cell-to-cell spread of infection provided by its dependence on growth in suspension. Viability was assayed via trypan blue exclusion at day 0, 7, 10, and 14. At day 14, both MOIs demonstrated less than 2.5% viable cells, as compared to 63.4% viability in the control cells.

Malignant/atypical Meningioma

All three malignant meningioma early passage tumor monolayers, including one hemangiopericytoma, were sensitive to dlsptk, with complete monolayer destruction evident from day 6 to day 9 at an MOI of $10^{-1}$ and in 11 days or less at an MOI of $10^{-3}$. The single atypical meningioma tested in monolayer was killed in 7 days by MOIs of $10^{-2}$ and $10^{-3}$.

Neurofibrosarcoma

Cytopathic effects were evident in all five neurofibrosarcomas at an MOI of $10^{-1}$, where monolayer destruction took from 4 to 13 days. Four of the five neurofibrosarcomas were also treated with an MOI of $10^{-3}$; in three, monolayer destruction took from 5 to 12 days. The remaining neurofibrosarcoma showed 75% cytopathogenicity at day 15, when the experiment was abandoned due to the appearance of control cell death, presumably from nutrient depletion.

In vitro Cytopathic Efficacy of dlsptk

| Tumor | Pathology | Cell line/ Tumor prep | MOI | ≥99% CPE (days) |
|---|---|---|---|---|
| Daoy | Medulloblastoma (glial-type) | CL | 0.1 | 4 |
|  |  |  | 0.001 | 4 |
| SNB40 | Medulloblastoma (glial-type) | CL | 0.1 | 4 |
|  |  |  | 0.001 | 11 |
| D283 | Medulloblastoma | CL (suspension) | 10 | * |
|  |  |  | 1 | ≤14 |
| PD | Mal. meningioma | TP | 0.1 | 9 |
|  |  |  | .001 | 11 |
| FZ | Mal. meningioma (HP) | TP | 0.1 | 7 |
|  |  |  | 0.001 | 10 |
| JC | Mal. meningioma | TP | 0.1 | 6 |
|  |  |  | 0.001 | 10 |
| BD | Atyp. meningioma | TP | 0.01 | 7 |
|  |  |  | .001 | 7 |
| NFS #3 | Neurofibrosarcoma | CL | 0.1 | 9 |
|  |  |  | 0.001 | 12 |
| NFS #4 | Neurofibrosarcoma | CL | 0.1 | 5 |
|  |  |  | 0.001 | 7 |
| NFS #5 | Neurofibrosarcoma | CL | 0.1 | 4 |
|  |  |  | 0.001 | 5 |
| NGS #7 | Neurofibrosarcoma | CL | 0.1 | 13 |
| Ch | Neurofibrosarcoma | TP | 0.1 | 10 |
|  |  |  | 0.001 | * |

Listed above are the tumors tested in vitro for cytopathic efficacy of HSV-1 thymidine kinase negative mutant dlsptk. All tumors were tested at MOIs of 0.1 and 0.001 except for the suspension cell line D283 Med which was tested at MOIs of 1 and 10 (further explanation in text).
1. Tumor prep = cells passaged from tumor specimen in vitro; not established cell lines.
2. MOI-multiplicity of infection.
3. CPE-cytopathic efficacy, or percent cells killed.
4. HP-hemangiopericytic type.
5. Maximum cytopathic efficacy of 97.8% reached in D283 Med when assessed at 14 days and 75% in Ch at MOI-.001 at 15 days. Both experiments could not be continued due to the appearance of control death from nutrient depletion.

Figure 3:
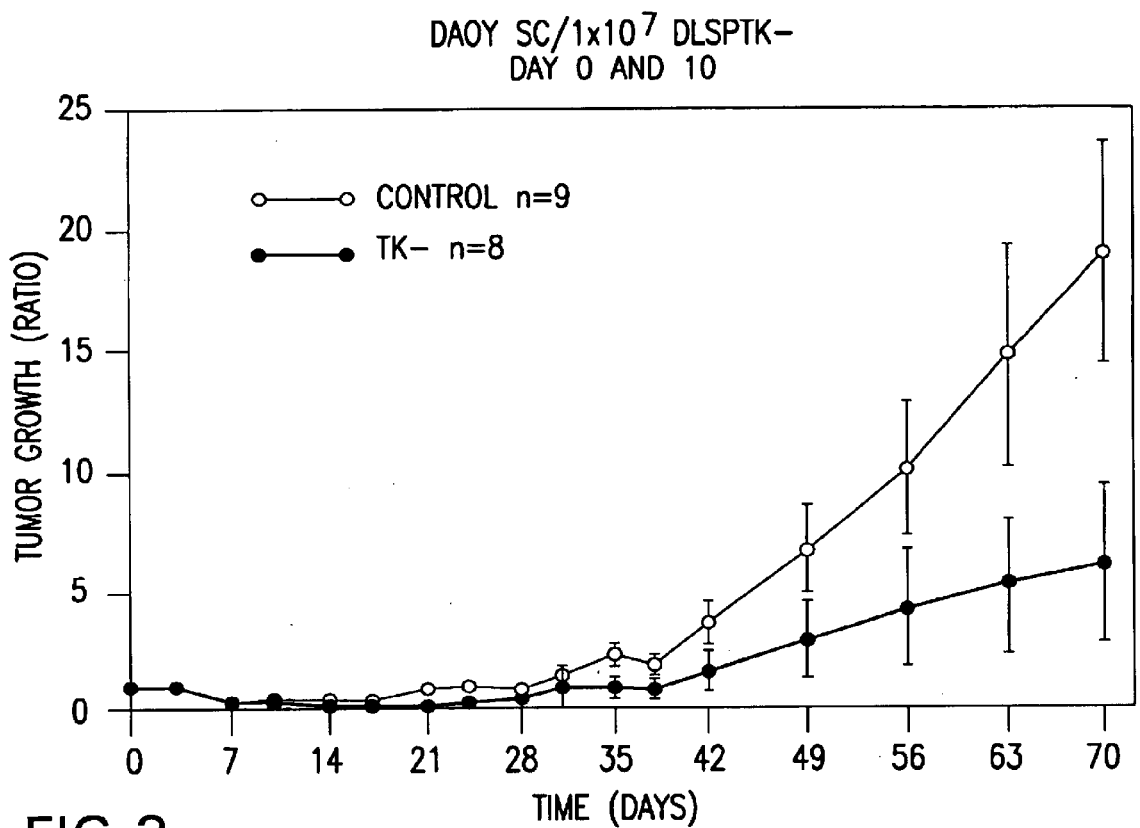
FIG. 3 shows a graph of the results of treatment of subcutaneous medulloblastomas with dlsptk at days 0 and 10. Mean tumor growth rate was significantly inhibited in dlsptk-treated tumors (growth ratio 5.96±3.30, mean±standard error of the mean) when compared to control tumors treated with DME+ (growth ratio 18.83±4.55) after 70 days. Additionally, a significant number of regressions was seen in the treated group, while none were observed in the control group.

In Vivo Xenografts dlsptk demonstrated anti-neoplastic effects against the medulloblastoma cell line Daoy when tested in subcutaneous xenografts. The mean growth ratio of tumors in the control animals was consistently greater than or equal to the mean growth ratio of tumors in the dlsptk-treated group. At day 70, the mean growth ratio for dlsptk-treated tumors was 32% of the mean growth ratio of untreated tumors (5.96±3.30 versus 18.83±4.55, mean±standard error of the mean). In the eight dlsptk-treated animals, three tumor regressions and one apparent cure were observed; there were no regressions in the nine control animals (See FIG. 3).

Discussion

These studies have demonstrated that the use of genetically-engineered viral therapy for the treatment of malignant nervous system tumors may be extended from malignant gliomas to other neoplasms, including medulloblastomas of different differentiation types, malignant or atypical meningiomas, and neurofibrosarcomas. Monolayer destruction was demonstrated in all tumors tested. In addition, intratumoral inoculation of dlsptk into subcutaneous xenografts of the medulloblastoma Daoy in nude mice resulted in a significant decrease in tumor growth rate in vivo, with fully 50% of treated tumors regressing, one of which was an apparent cure.

In this Example, as in Example 1 with gliomas, the mutant dlsptk was selected because it retains ability to kill dividing tumor cells but possesses attenuated neuropathogenicity.

As shown in Example 3 below, other viral mutants, which retain the ability to kill dividing tumor cells but possess attenuated neuropathogenicity, also prove efficacious in the treatment of a nervous system tumor.

EXAMPLE 3

Four different HSV mutants known to replicate well in cultured cells but which demonstrate decreased neurovirulence were investigated. Two, Ara A$^r$9 and Ara A$^r$13, contain point mutations in the gene encoding viral DNA polymerase. These mutants are hypothesized to be replication-compromised in brain, due to a lower affinity for deoxynucleoside phosphates which are presumed to be at low concentration in brain. The mutants Ara A$^r$9 and Ara$^r$13 are disclosed in Coen et al., *J. virol.* 41(3):909–918 (1982); Coen et al., *J. Virol.* 53(2):477–488 (1985); Gibbs et al., *Proc. Natl. Acad. Sci. USA* 82:7969–7973 (1985), Field et al., *J. Virol.* 60(1):286–289 (1986); Hall et al., *Virology* 132:26–37 (1984); and Gibbs et al., *Proc. Natl. Acad. Sci. USA* 85:6672–6676 (1988)). Another mutant, RE6, is an intertypic recombinant (HSV-1 and HSV-2) with a lesion conferring attenuation mapping to the inverted repeat in the long segment of the HSV genome. The mutant RE6 is disclosed in Thompson et al, *Virology* 172:435–440 (1989) and Thompson et al., *Virology* 131:171–179 (1983). The final mutant, R3616, contains a double mutation in both copies of the γ-34.5 gene, which lies in the same repeat sequence. The mutant R3616 is disclosed in Chou et al., *Science* 250:1252–1266 (1990).

These four HSV mutants were tested for their suitability in treating neoplastic cells.

In Vitro Assay of Cytotoxicity

In cell culture, viral mutants (Ara $A^r9$, Ara $A^r13$, R3616 and RE6) were applied to a human glioma line, U87, as described in Example 1. Viruses were applied at two multiplicities of infection (MOI), $10^{-1}$ and $10^{-3}$. All viruses destroyed the glioma monolayers via spreading infection at both MOIs tested, with time to complete monolayer destruction ranging from 4 days for Ara $A^r9$ at an MOI-$10^{-1}$, to 14 days for R3616 at an MOI-$10^{-3}$. To further demonstrate the cytopathic efficacy of the HSV mutants against human glioma cells, short-term glioma cultures were established by explanting two human glioblastomas in DME+, which were then tested at second passage as previously described. All monolayers were destroyed in 15 days or less by all viruses at both MOIs tested ($10^{-1}$, $10^{-3}$).

Assay of the Effects of HSV Mutants on Human Gliomas in Vivo

To test the effects of these HSV mutants on human gliomas in vivo, we implanted minced pieces (1 mm³ or smaller) of U87 tumor into nude mice subcutaneously (tumor pieces were obtained from nude mice previously injected subcutaneously with cultured U87 cells). Growing tumors ($\geq 8$ mm in diameter) were evident between weeks 4 and 5, at which time the mice were divided into two groups of 7 to 10 animals per group. Mice in group one were designated controls and received intraneoplastic injections of 50–60 μl of DME+; mice in group two were designated treatment animals and received similar intraneoplastic injections of virus suspended in DME+. Similar experiments were conducted for each of the four virus mutants at various doses (maximum doses were limited by titers of stock obtainable for each mutant; see Table 2).

TABLE 2

Viral Inhibition of subcutaneous U87 tumor growth

| Mutant | Dose (pfu) | Number of Doses | Growth ratio comparison | Statistical Significance |
|---|---|---|---|---|
| Ara $A^r9$§ | $5 \times 10^6$ | Day 0, 14 | 0.79 | N.S. |
| Ara $A^r13$ | $1 \times 10^7$ | Day 0, 14 | 0.94 | N.S. |
| | $2.5 \times 10^7$ | Day 0, 14 | ? | p < ? |
| RE6 | $1 \times 10^7$ | Day 0, 14 | 0.33 | p < 0.05 |
| | $1 \times 10^8$ | Day 0 only | 0.42 | p < 0.05 |
| R3616 | $1 \times 10^7$ | Day 0, 14 | 0.75 | N.S. |

TABLE 2-continued

Viral Inhibition of subcutaneous U87 tumor growth

| Mutant | Dose (pfu) | Number of Doses | Growth ratio comparison | Statistical Significance |
|---|---|---|---|---|
| | $1 \times 10^8$ | Day 0 only | 0.47 | N.S. |
| | $2 \times 10^9$ | Day 0, 14 | ? | p < ? |
| dlsptk | $1 \times 10^7$ | Day 0, 14 | 0.21 | p < 0.05 |

Figure 4:
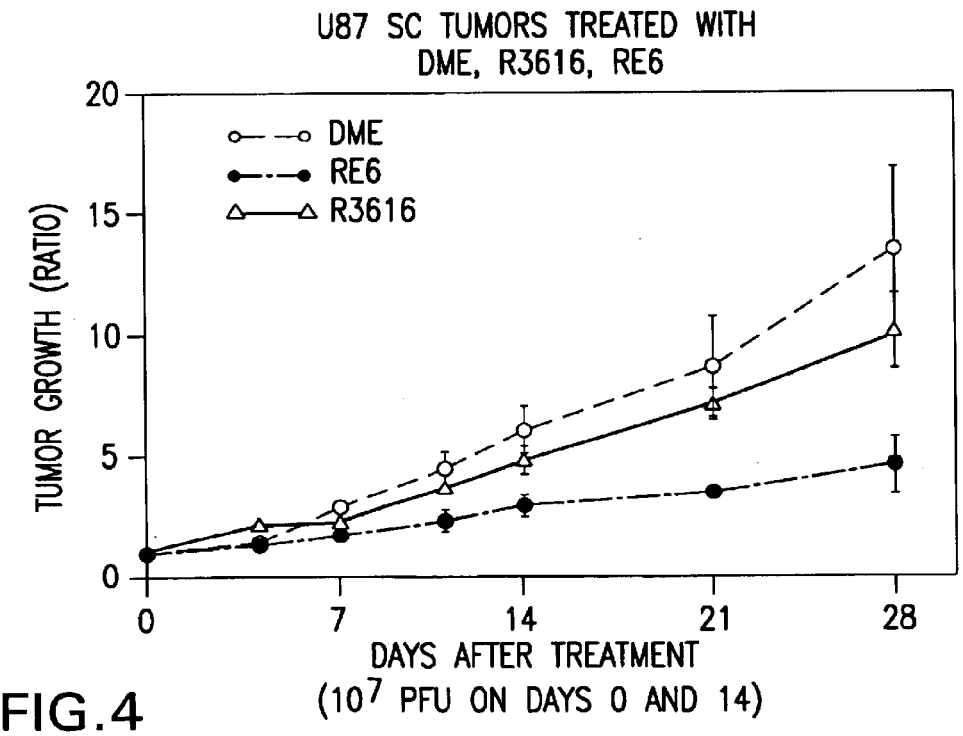
FIG. 4 shows the effect of inoculating $10^7$ pfu (on days 0 and 14) of DME (control), RE6 and R3616 on tumor growth. At this dose regimen, RE6 was effective, while R3616 and Ara A'13 were not.
Figure 5:
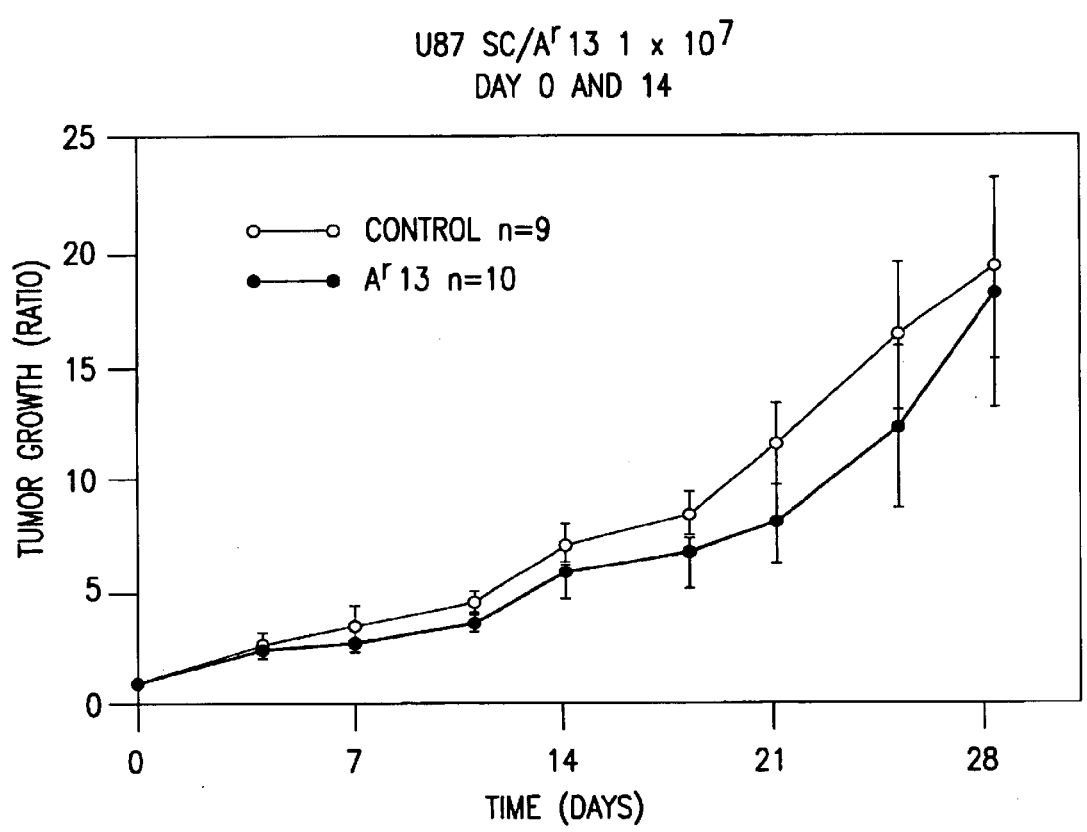
FIG. 5 shows the effect of inoculating $10^7$ pfu (on days 0 and 14) of DME and Ara A'13. Ara A'13 was not effective at this dosage.
Figure 6:
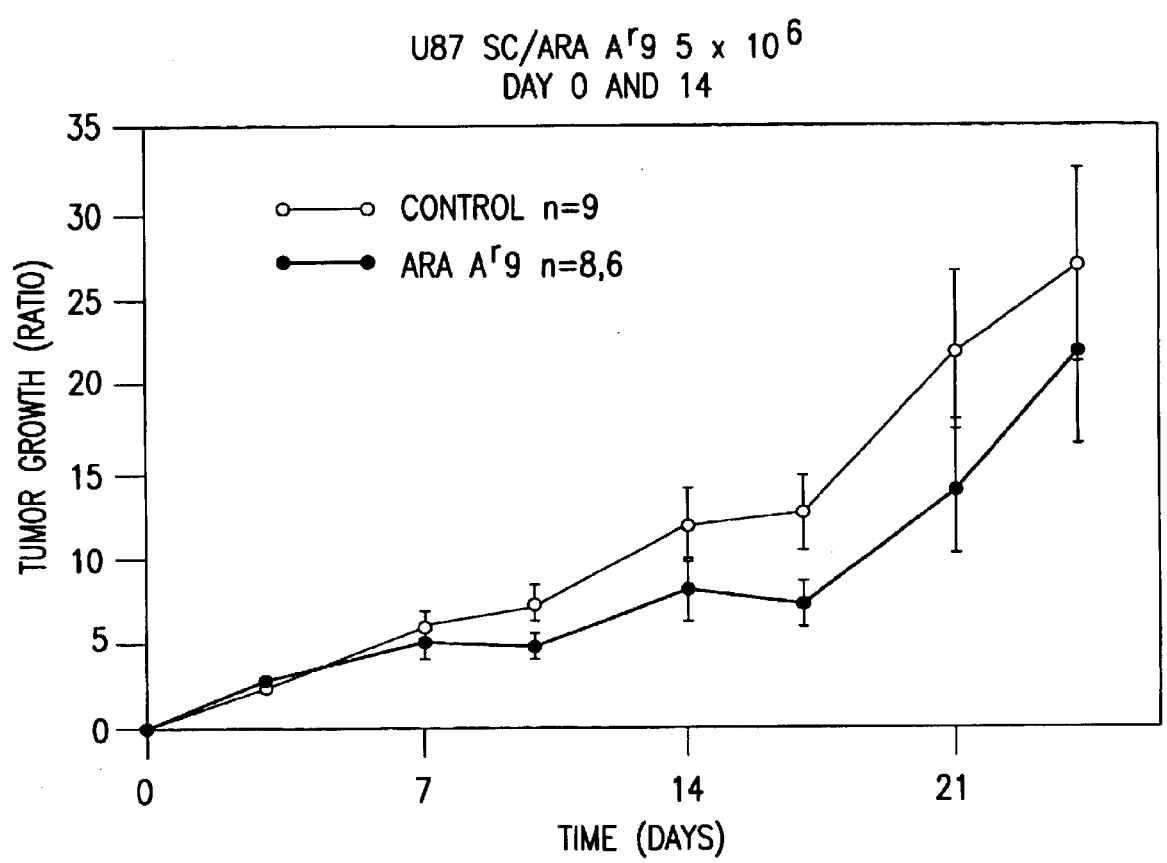
FIG. 6 shows that at a dosage of $5 \times 10^6$ pfu, Ara A'9 did not demonstrate effective inhibition of tumor growth.
Figure 7:
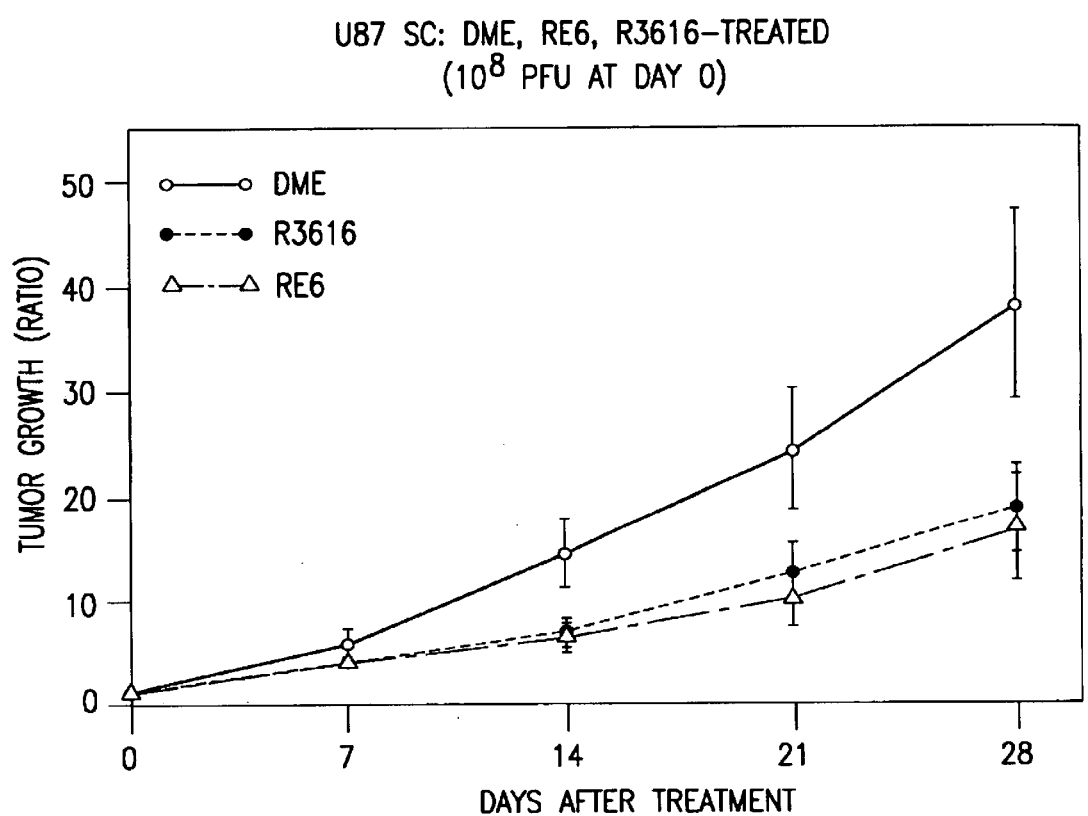
FIG. 7 shows that RE6 effectively inhibited tumor growth when administered at a regimen of one dose at $10^8$ pfu, inoculated at day 0.

Table lists viral mutants and their performance as inhibitors of tumor growth at tested doses in subcutaneous U87 gliomas implanted in nude mice. Mice were injected intraneoplastically with virus suspended in 0.05 ml DME+ (see text). Growth ratio comparisons are the ratio of the treated group growth ratio mean to the control group growth radio mean at 28 days after initial treatment; a value of less than one demonstrates inhibition of tumor growth by the virus. Experiments could generally not be carried out longer than 28 days due to death from tumor burden in the control animals. Statistical significance as calculated by one-sided Wilcoxon rank test is listed in the final column. Values greater than 0.05 are listed as not significant (N.S.). Values from previous studies are given for dlsptk for comparison purposes, along with values given from a study of dlsptk heat-inactivated by boiling for ten minutes. §Study discontinued at 24 days due to deaths from tumor burden.

dlsptk, the only previously tested mutant, had shown significant tumor inhibition at $10^7$ pfu inoculated on days 0 and 14. At the same dose regimen, RE6 was effective, while R3616 and Ara $A^r13$ were not (FIGS. 4 and 5). At the highest inocula tested ($5 \times 10^6$ pfu), Ara $A^r9$ never demonstrated effective inhibition of tumor growth (FIG. 6); a shorter study of dlsptk at this dose showed statistically significant reduction of tumor growth at 14 days (data not shown). At higher doses, all three mutants tested showed significant tumor growth inhibition. Ara $A^r13$ demonstrated reductions in tumor growth at a dose of $2.5 \times 10^7$ pfu given in the same dosing schedule. R3616 showed statistically significant tumor growth inhibition in two doses of $2 \times 10^9$ pfu. To determine if one dose was adequate to cause inhibition of tumor growth, we tested RE6 and R3616 at $10^8$ pfu, inoculated at day 0. Only RE6 was effective when given in this regimen (FIG. 7).

Figure 8:
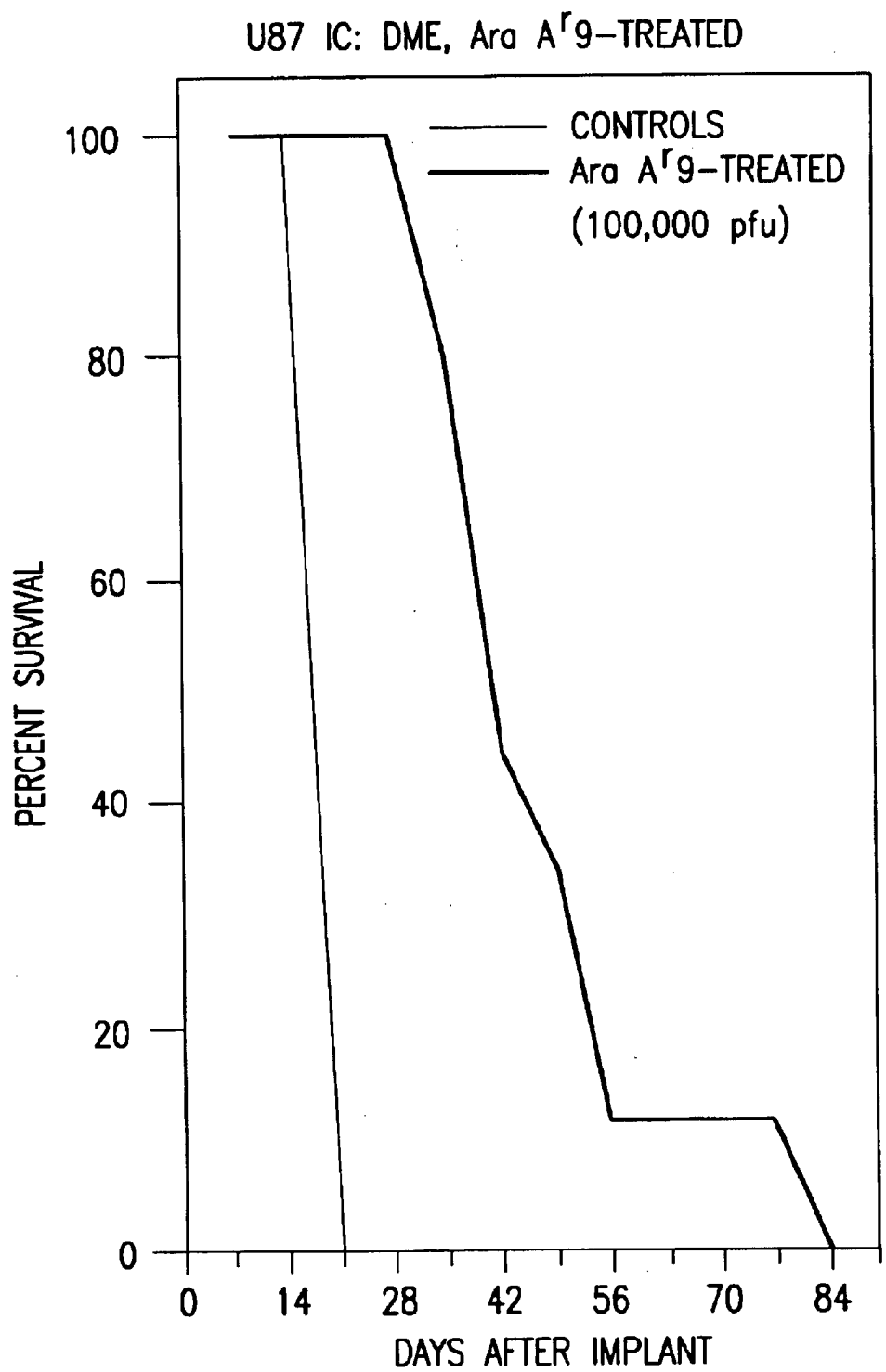
FIG. 8 shows that mice treated with intracranial inoculations of $10^5$ pfu of Ara A'9 all died within eleven days of inoculation (21 days after implant), whereas the controls lived a median of 45 days after implant.
Figure 9:
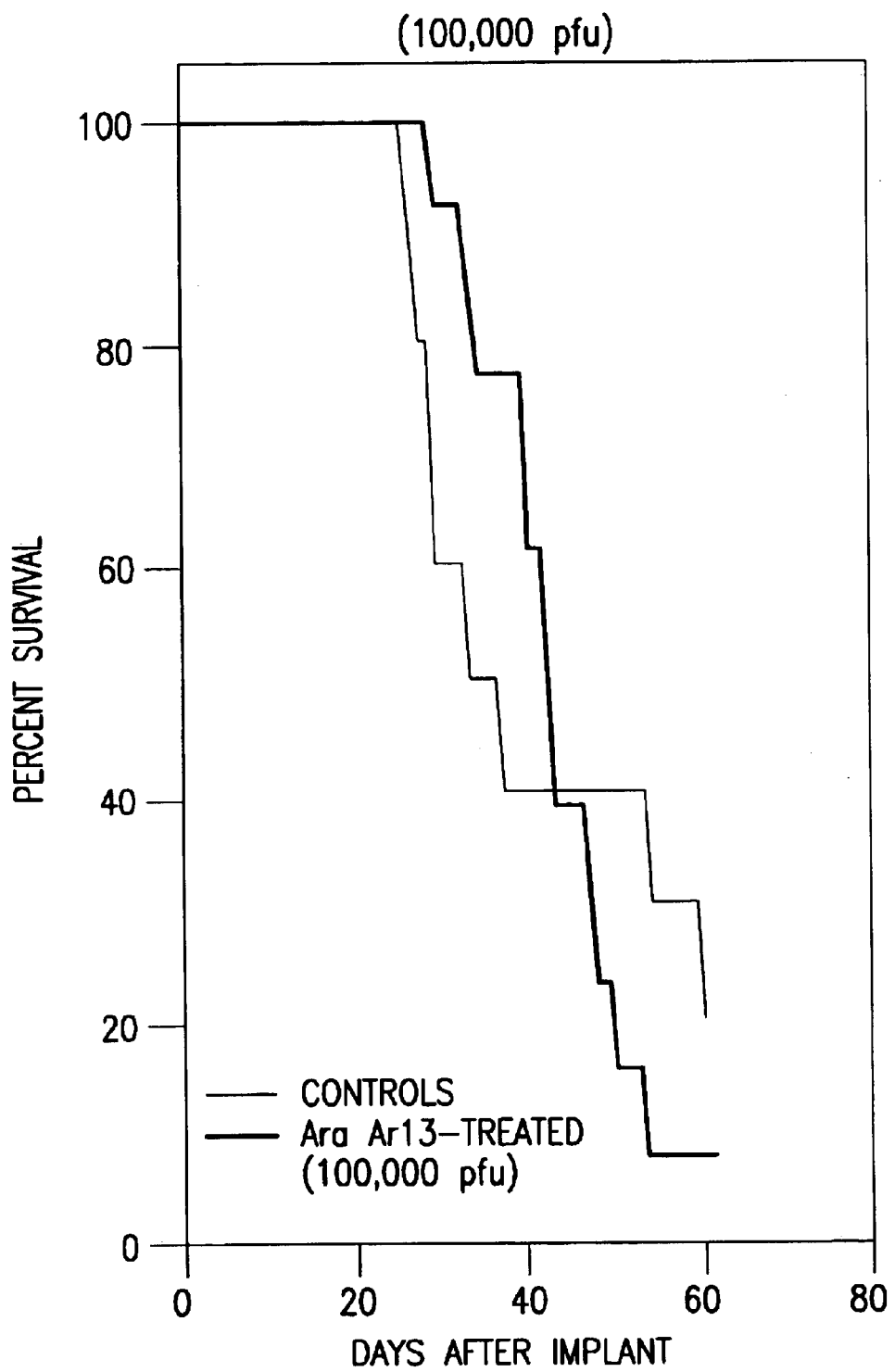
FIG. 9 shows that mice treated with intracranial inoculation of $10^5$ pfu of Ara A'13 demonstrated a decrease in median days of survival when compared to controls without a statistically significant increase in long term survivors.

To evaluate the safety and efficacy of each virus in treating intracerebral gliomas, we stereotactically inoculated nude mice in the right frontal lobe with $2$–$4 \times 10^5$ U87 cells. Previous experiments have consistently demonstrated 100% mortality in untreated animals receiving such inoculations. For treatment with Ara $A^r9$ and Ara $A^r13$, animals were then randomly divided into control and treatment groups. Ten days after tumor implantation, control animals received intracranial inoculations of 2 μl DME+, while treated animals received intracranial inoculations of $10^5$ pfu of selected virus suspended in 2 μl DME+. Group sizes ranged from eight to thirteen animals for all intracranial experiments. Mice treated with intracranial inoculations of $10^5$ pfu of Ara $A^r9$ all died within 11 days of virus treatment (21 days after implant), whereas the controls lived a median of 45 days after implant with the final death occurring 12 weeks after implantation (FIG. 8). Mice treated with Ara $A^r13$ also demonstrated a decrease in median days of survival when compared to controls without a statistically significant increase in long-term survivors (FIG. 9).

Figure 10:
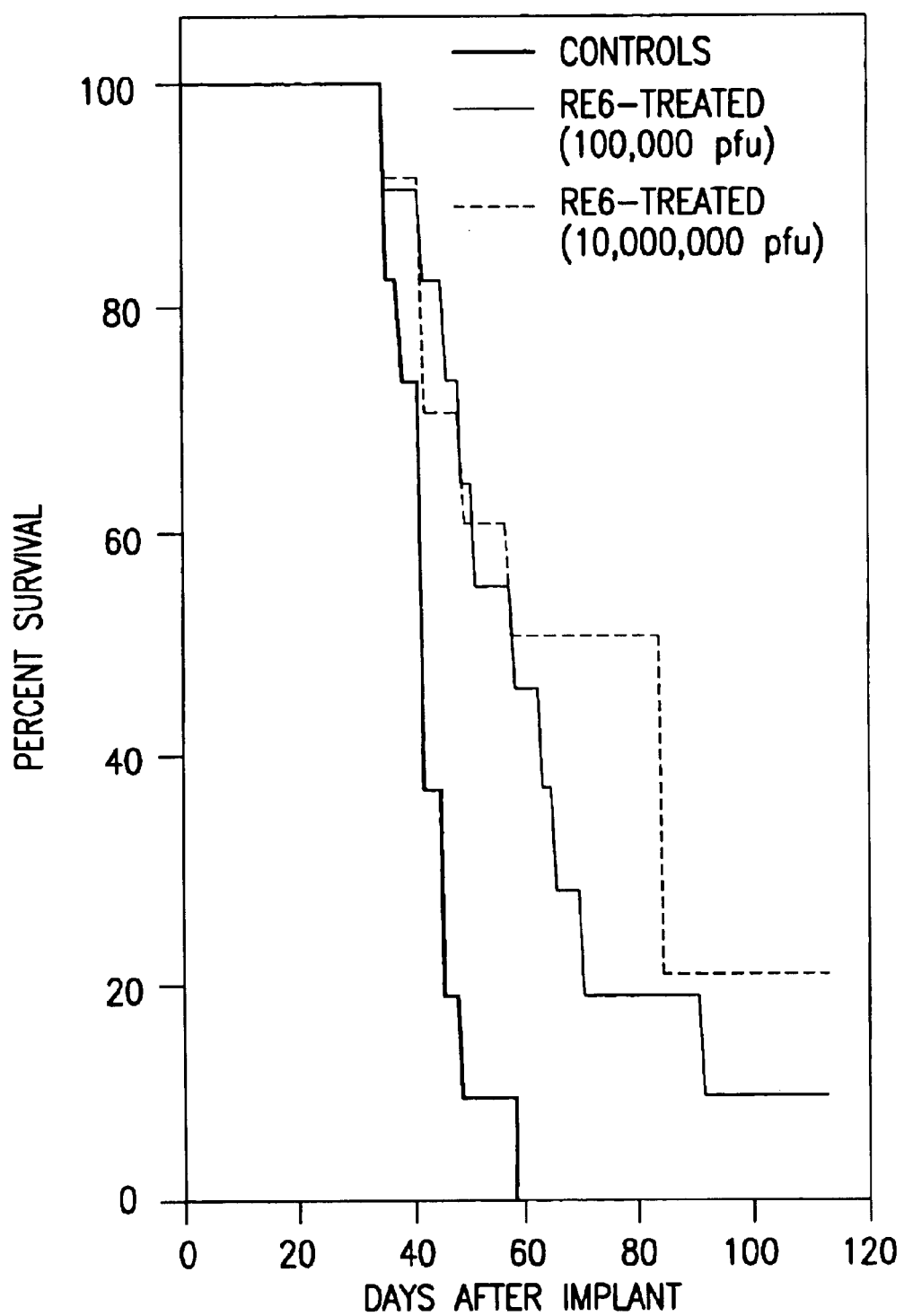
FIG. 10 shows that mice treated with intracranial inoculation of $10^5$ pfu and $10^7$ pfu of RE6 exhibited statistically significant increase in survival when compared to controls. Median survival was 42 days for control mice. Median survival was 58 days for mice inoculated with $10^5$ pfu of RE6. Median survival was 84 days for mice treated with $10^7$ pfu of RE6.
Figure 11:
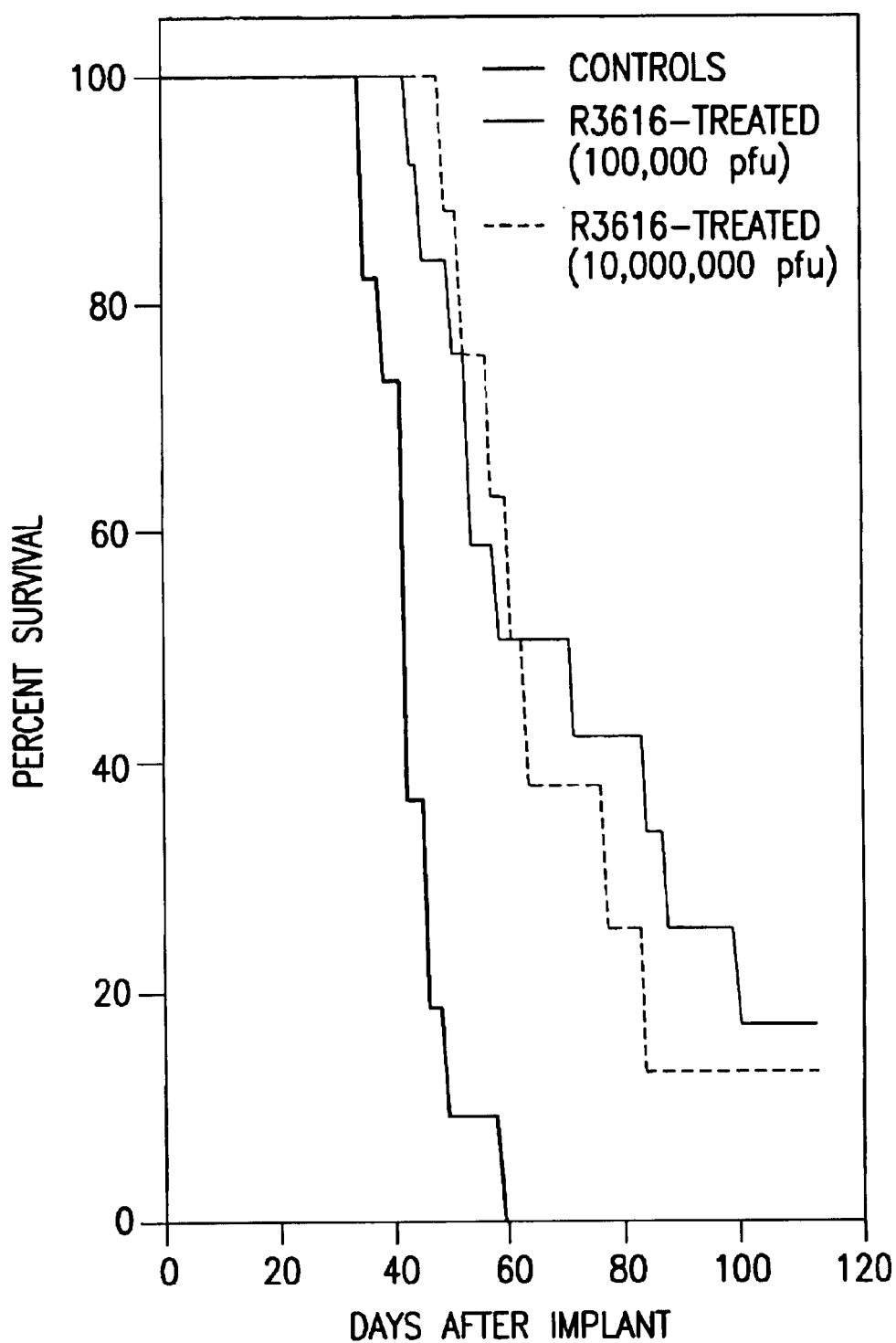
FIG. 11 shows that mice treated with intracranial inoculations of $10^5$ pfu and $10^7$ pfu of R3616 exhibited statistically significant increases in survival when compared to controls. Median survival for control mice was 42 days. Median survival was 71 days for mice inoculated with $10^5$ pfu of R3616. Median survival was 63 days for mice inoculated with $10^7$ pfu of R3616.

For treatment with RE6 and R3616, a similar protocol was followed except animals were randomly divided into three groups. Ten days after tumor implantation, the control group received intracranial inoculations of 6 μl DME+ as above, the second group received intracranial inoculations of $10^5$ pfu of the test virus and the third group received intracranial inoculations of $10^7$ pfu of the test virus, each suspended in 6 μl DME+. Higher doses were attempted with these two viruses as earlier published reports demonstrated no fatalities in mice without intracranial tumors receiving intracranial inoculations at these doses. Statistically significant increases in survival were seen in all four groups of virus-treated animals compared with controls (median survival was 42 days for control animals for all experiments): RE6, $10^5$ pfu, median survival 58 days (log-rank statistic <0.004; FIG. 10); RE6, $10^7$ pfu, median survival 84 days (log-rank statistic <0.007; FIG. 10); R3616, $10^5$ pfu, median survival 71 days (log-rank statistic <0.0003; FIG. 11). There were no statistically significant differences in survival between treated groups. In none of the four treated groups did any deaths occur prior to those in the control group; percent survival in each of the treated groups was at all times greater than or equal to percent survival in the control group. After 120 days, all six surviving animals were sacrificed (RE6 $10^7$ and R3616 $10^5$), two each; RE6 $10^5$ and R3616, one each). All appeared neurologically normal at this time. The brains were fixed, serially sectioned at 7 μm intervals, stained with hematoxylin and eosin, and microscopically examined. Some residual tumor cells were present, but no evidence of encephalitis was visible.

Discussion

As demonstrated in Example 1 with dlsptk, and confirmed with Example 3, recombinant and genetically-engineered viruses can be constructed to destroy glioma cells both in vitro and in vivo. Whereas Example 1 demonstrates inhibition of tumor growth and increased survival in intracranially-implanted tumors, Example 3 confirms that 1) these effects can be duplicated with different HSV mutants which retain thymidine kinase proficiency, and 2) with some viral mutations, early encephalitic deaths due to viral treatment can be eliminated. An additional safety advantage of RE6, R3616, and Ara A$^r$13 over dlsptk as potential therapeutic agents is retained sensitivity to ganciclovir a commonly used anti-herpetic agent.

Modifications of the above-described modes for carrying out the invention that are obvious to persons of skill in medicine, immunology, hybridoma technology, pharmacology, and/or related fields are intended to be within the scope of the following claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for selectively killing nervous system tumor cells in a mammal, said method comprising:
    a) directly administering to a tumor in said mammal a mutated herpes simplex virus, wherein said mutated herpes simplex virus comprises a mutation in the γ-34.5 gene; and wherein said mutated herpes simplex virus exhibits decreased virulence in normal neural cells while maintaining cytopathic effects in said nervous system tumor cells; and wherein said mutated herpes simplex virus is capable of selective replication in said nervous system tumor cells; and thereby
    b) killing said nervous system tumor cells.

2. The method of claim 1 wherein the mammal is human.

3. The method of claim 1 wherein the tumor is selected from the group consisting of astrocytoma, oligodendroglioma, meningioma, neurofibroma, glioblastoma, ependymoma, Schwannoma, neurofibrosarcoma, and medulloblastoma.

4. The method of claim 3, wherein the tumor is a glioblastoma.

5. The method of claim 3, wherein the tumor is a medulloblastoma.

6. The method of claim 3, wherein the tumor is a meningioma.

7. The method of claim 3, wherein the tumor is a neurofibrosarcoma.

8. The method of claim 1, wherein said mutated herpes simplex virus is R3616.

9. A method for inhibiting growth of nervous system tumor cells, said method comprising:
    a) infecting said tumor cells with a mutated herpes simplex virus, wherein said mutated herpes simplex virus comprises a mutation in the γ-34.5 gene; and wherein said mutated herpes simplex virus exhibits decreased virulence in normal neural cells while maintaining cytopathic effects in said nervous system tumor cells, and wherein said mutated herpes simplex virus is capable of selective replication in said nervous system tumor cells; and thereby
    b) inhibiting growth of said nervous system tumor cells.

10. The method of claim 9 wherein the tumor is selected from the group consisting of glioblastoma, medulloblastoma, meningioma, neurofibrosarcoma, astrocytoma, oligodendroglioma, neurofibroma, ependymoma and Schwannoma.

11. The method of claim 9, wherein said mutated herpes simplex virus is R3616.

12. A method for selectively killing nervous system tumor cells in a mammal, said method comprising:
    a) directly administering to a tumor in said animal a mutated herpes simplex virus, wherein said mutated herpes simplex virus is an intertypic HSV-1 and HSV-2 recombinant with a lesion conferring attenuation mapping to the inverted repeat in the long segment of the HSV genome; and wherein said mutated herpes simplex virus exhibits decreased virulence in normal neural cells while maintaining cytopathic effects in said nervous system tumor cells; and wherein said mutated herpes simplex virus is capable of selective replication in said nervous system tumor cells; and thereby
    b) killing said nervous sytem tumor cells.

13. The method of claim 12, wherein the intertypic recombinant is RE6.

14. The method of claim 12, wherein said mammal is human.

15. The method of claim 12, wherein the tumor is selected from the group consisting of astrocytoma, oligodendroglioma, meningioma, neurofibroma, glioblastoma, ependymoma, Schwannoma, neurofibrosarcoma, and medulloblastoma.

16. The method of claim 15, wherein the tumor is a glioblastoma.

17. The method of claim 15, wherein the tumor is a medulloblastoma.

18. The method of claim 15, wherein the tumor is a meningioma.

19. The method of claim 15, wherein the tumor is a neurofibrosarcoma.

20. A method for inhibiting growth of nervous system tumor cells, said method comprising:
    a) infecting said tumor cells with a mutated herpes simplex virus, wherein said mutated herpes simplex virus is an intertypic HSV-1 and HSV-2 recombinant with a lesion conferring attenuation mapping to the inverted repeat in the long segment of the HSV genome; and wherein said mutated herpes simplex virus exhibits decreased virulence in normal neural cells while maintaining cytopathic effects in said nervous system tumor cells, and wherein said mutated herpes simplex virus is capable of selective replication in said nervous system tumor cells; and thereby b) inhibiting growth of said nervous system tumor cells.

21. The method of claim 20, wherein the intertypic recombinant is RE6.

22. The method of claim 20, wherein the tumor is selected from the group consisting of astrocytoma, oligodendroglioma, meningioma, neurofibroma, glioblastoma, ependymoma, Schwannoma, neurofibrosarcoma, and medulloblastoma.

23. A method for selectively killing nervous system tumor cells in a mammal, said method comprising:
  a) directly administering to a tumor in said mammal a mutated herpes simplex virus, wherein said mutated herpes simplex virus comprises a mutation in the thymidine kinase gene, wherein said mutation does not impair UL24 gene function; and wherein said mutated herpes simplex virus exhibits decreased virulence in normal neural cells while maintaining cytopathic effects in said nervous system tumor cells; and wherein said mutated herpes simplex virus is capable of selective replication in said nervous system tumor cells; and thereby
  b) killing said nervous system tumor cells.

24. The method of claim 23, wherein said mutated herpes simplex virus is dlsptk.

25. The method of claim 23, wherein said mammal is human.

26. The method of claim 23, wherein the tumor is selected from the group consisting of astrocytoma, oligodendroglioma, meningioma, neurofibroma, glioblastoma, ependymoma, Schwannoma, neurofibrosarcoma, and medulloblastoma.

27. The method of claim 1 wherein the tumor is a glioblastoma.

28. The method of claim 27, wherein the tumor is a medulloblastoma.

29. The method of claim 27, wherein the tumor is a meningioma.

30. The method of claim 27, wherein the tumor is a neurofibrosarcoma.

31. A method for inhibiting growth of nervous system tumor cells, said method comprising:
  a) infecting said tumor cells with a mutated herpes simplex virus, wherein said mutated herpes simplex virus comprises a mutation in the thymidine kinase gene, wherein said mutation does not impair UL24 gene function; and wherein said mutated herpes simplex virus exhibits decreased virulence in normal neural cells while maintaining cytopathic effects in said nervous system tumor cells, and wherein said mutated herpes virus is capable of selective replication in said nervous system tumor cells; and thereby
  b) inhibiting growth of said nervous system tumor cells.

32. The method of claim 31, wherein said mutated herpes simplex virus is dlsptk.

33. The method of claim 31, wherein the tumor is selected from the group consisting of astrocytoma, oligodendroglioma, meningioma, neurofibroma, glioblastoma, ependymoma, Schwannoma, neurofibrosarcoma, and medulloblastoma.

34. A method for selectively killing nervous system tumor cells in a mammal, said method comprising:
  a) directly administering to a tumor in said mammal a mutated herpes simplex virus, wherein said mutated herpes simplex virus comprises a mutation in the DNA polymerase gene; and wherein said mutated herpes simplex virus exhibits decreased virulence in normal neural cells while maintaining cytopathic effects in said nervous system tumor cells; and wherein said mutated herpes simplex virus is capable of selective replication in said nervous system tumor cells; and thereby
  b) killing said nervous system tumor cells.

35. The method of claim 34, wherein said mutated herpes simplex virus is AraA$^r$13.

36. The method of claim 34, wherein said mammal is human.

37. The method of claim 34, wherein the tumor is selected from the group consisting of astrocytoma, oligodendroglioma, meningioma, neurofibroma, glioblastoma, ependymoma, Schwannoma, neurofibrosarcoma, and medulloblastoma.

38. The method of claim 37, wherein the tumor is a glioblastoma.

39. The method of claim 37, wherein the tumor is a medulloblastoma.

40. The method of claim 37, wherein the tumor is a meningioma.

41. The method of claim 37, wherein the tumor is a neurofibrosarcoma.

42. A method for inhibiting growth of nervous system tumor cells, said method comprising:
  a) infecting said tumor cells with a mutated herpes simplex virus, wherein said mutated herpes simplex virus comprises a mutation in the DNA polymerase gene; and wherein said mutated herpes simplex virus exhibits decreased virulence in normal neural cells while maintaining cytopathic effects in said nervous system tumor cells, and wherein said mutated herpes virus is capable of selective replication in said nervous system tumor cells; and thereby
  b) inhibiting growth of said nervous system tumor cells.

43. The method of claim 42, wherein said mutated herpes simplex virus is AraA$^r$13.

44. The method of claim 42, wherein the tumor is selected from the group consisting of astrocytoma, oligodendroglioma, meningioma, neurofibroma, glioblastoma, ependymoma, Schwannoma, neurofibrosarcoma, and medulloblastoma.

* * * * *

UNITED STATES PATENT AND TRADEMARK OFFICE
CERTIFICATE OF CORRECTION

PATENT NO.       : 6,770,274 B1
APPLICATION NO.  : 08/272516
DATED            : August 3, 2004
INVENTOR(S)      : Martuza et al.

Page 1 of 1

It is certified that error appears in the above-identified patent and that said Letters Patent is hereby corrected as shown below:

On the title page,
[*] delete "Subject to any disclaimer, the term of this patent is extended or adjusted under 35 U.S 154(b) by 1,825 days."

Signed and Sealed this

Tenth Day of October, 2006

JON W. DUDAS
*Director of the United States Patent and Trademark Office*